(12) United States Patent
Katano

(10) Patent No.: US 10,870,100 B2
(45) Date of Patent: Dec. 22, 2020

(54) ION WIND GENERATION DEVICE

(71) Applicant: Katano Kogyo Co., Ltd., Yokohama (JP)

(72) Inventor: Akio Katano, Yokohama (JP)

(73) Assignee: Katano Kogyo Co., Ltd., Yokohama (JP)

( * ) Notice: Subject to any disclaimer, the term of this patent is extended or adjusted under 35 U.S.C. 154(b) by 206 days.

(21) Appl. No.: 16/089,005

(22) PCT Filed: Feb. 8, 2017

(86) PCT No.: PCT/JP2017/004602
§ 371 (c)(1),
(2) Date: Sep. 27, 2018

(87) PCT Pub. No.: WO2017/169153
PCT Pub. Date: Oct. 5, 2017

(65) Prior Publication Data
US 2019/0111405 A1    Apr. 18, 2019

(30) Foreign Application Priority Data

Mar. 30, 2016  (JP) ................. 2016-068853

(51) Int. Cl.
| | |
|---|---|
| *B01J 19/08* | (2006.01) |
| *A61L 9/22* | (2006.01) |
| *H01T 19/04* | (2006.01) |
| *H01T 23/00* | (2006.01) |
| *A61L 2/14* | (2006.01) |

(Continued)

(52) U.S. Cl.
CPC .............. *B01J 19/088* (2013.01); *A61L 2/14* (2013.01); *A61L 2/202* (2013.01); *A61L 9/046* (2013.01);

(Continued)

(58) Field of Classification Search
CPC .............. B01J 19/088; B01J 2219/0833; B01J 2219/0849; B01J 2219/0896; A61L 2/14;

(Continued)

(56) References Cited

U.S. PATENT DOCUMENTS

| | | | |
|---|---|---|---|
| 8,778,273 | B2 | 7/2014 | Merbahi et al. |
| 2016/0111859 | A1 | 4/2016 | Katano |

FOREIGN PATENT DOCUMENTS

| | | |
|---|---|---|
| JP | H6-181087 A | 6/1994 |
| JP | 2003-074926 A | 3/2003 |

(Continued)

OTHER PUBLICATIONS

Extended European search report dated Feb. 19, 2020 for the corresponding EP application No. 17773701.2.

(Continued)

*Primary Examiner* — Xiuyu Tai
(74) *Attorney, Agent, or Firm* — Muncy, Geissler, Olds & Lowe, P.C.

(57) ABSTRACT

Provided is an ion wind generation device which is capable of providing a wide range of ion delivery and providing ion wind having a reduced ozone concentration near a nozzle without use of a filter or the like.

The ion wind generation device includes an electrode pair including a discharge electrode body having a discharge portion and a counter electrode body having a plurality of end portions, and generates ion wind by corona discharge that occurs due to a potential difference generated between the discharge portion and the end portions. The end portions are located spaced apart from one another in a single plane and disposed around an axis of the discharge electrode body in the single plane or disposed along a line in the single plane.

18 Claims, 26 Drawing Sheets

(51) Int. Cl.
*A61L 2/20* (2006.01)
*A61L 9/04* (2006.01)
*C01B 13/11* (2006.01)

(52) U.S. Cl.
CPC .............. *A61L 9/22* (2013.01); *C01B 13/115* (2013.01); *H01T 19/04* (2013.01); *H01T 23/00* (2013.01); *B01J 2219/0833* (2013.01); *B01J 2219/0849* (2013.01); *B01J 2219/0896* (2013.01); *C01B 2201/22* (2013.01)

(58) Field of Classification Search
CPC . A61L 2/202; A61L 9/046; A61L 9/22; C01B 13/115; C01B 2201/22; H01T 19/04; H01T 23/00; H01T 19/02; B60H 3/0078; F24F 2003/1685; F24F 2221/28; F24F 3/166; F24F 2003/1682; F24F 7/013; F25D 23/003; F25D 2317/0416; F25D 17/042; B03C 3/41; B03C 3/383; B03C 2201/06; B03C 2201/10; B03C 3/38; Y10T 428/24802; Y02P 20/133
See application file for complete search history.

(56) References Cited

FOREIGN PATENT DOCUMENTS

| | | | |
|---|---|---|---|
| JP | 2003-342005 | A | 12/2003 |
| JP | 2004-018348 | A | 1/2004 |
| JP | 3100754 | U | 5/2004 |
| JP | 2005-013831 | A | 1/2005 |
| JP | 2009-123564 | A | 6/2009 |
| JP | 3155540 | U | 11/2009 |
| JP | 5461736 | B1 | 4/2014 |
| JP | 2015-216032 | A | 12/2015 |
| RU | 2430742 | C1 | 10/2011 |
| WO | WO 2014/184984 | * | 11/2014 |
| WO | 2015/173977 | A1 | 11/2015 |

OTHER PUBLICATIONS

International Preliminary Report on Patentability of PCT/JP2017/004602 dated Oct. 11, 2018.

* cited by examiner

ION WIND GENERATION DEVICE

TECHNICAL FIELD

The present invention relates to a device for generating ion wind by corona discharge. More particularly, the present invention is directed to an ion wind generation device capable of providing ion wind having a reduced ozone concentration. Further, in a certain aspect, the present invention relates to a device and method for sterilizing and deodorizing a target object such as waste, and in particular, to a device and method for sterilizing and deodorizing the target object by causing corona discharge to occur in a space that is separate from a space in which the target object is placed, generating ions, and supplying ion wind to the space in which the target object is placed. More specifically, the present invention relates to an environmental device for sterilization and deodorization, designed to be equipped at a high airtight box, for example, a disposal box for garbage, diaper or the like, a box for a disposed odor of a garbage disposer, a box for receiving shoes, boots or the like, a toilet and a toilet tank, a high airtight container equipped with a refrigerating device and a vehicle equipped with a refrigerating device, a refrigerator, an indoor/in-vehicle air conditioner, or the like.

BACKGROUND ART

Due to aging of the society, there has been a high demand for a disposal box for diapers and the like in proportion to the population who need nursing care. However, the offensive odor that is released every time the box is opened gives a discomfort or burden to a caregiver and the ambient, and also it is unsanitary. In homes and restaurants where garbage storage boxes are present, the offensive odor caused by growth of bacteria that is released every time the boxes are opened also puts a large burden on housewives and relevant workers. As the use of garbage disposer increases due to development of biotechnology, offensive odor released around the garbage disposer during operation has become a very serious problem. In addition, transportation by transport containers, trucks, and the like are mainly used for international and domestic distribution of frozen, refrigerated, and normal-temperature products, and the like. Such containers and trucks have a number of types, such as marine containers, on-land containers, container-type trucks, and the like that are equipped with air conditioners. However, residual odor of loaded products and musty odor in air conditioners have become problematic. Further, air conditioners for storehouses, refrigerators, or indoor/in-vehicle spaces have the problem of offensive odor depending on the usage conditions of stored materials.

As a solution to the above problem, a simplified sterilizer/deodorizer, such as a spray type, has been proposed. However, when such a simplified sterilizer/deodorizer is used in a waste box or a garbage storage box, offensive odor is released when the box is opened. Further, another problem arises when the simplified sterilizer/deodorizer (of, for example, dispersion or cyclic sterilization type) is used in an air conditioner. For example, the air conditioner has a part that cannot be cleaned, and when abnormal odor or musty order is left even if the air conditioner is cleaned, offensive odor transfers to subsequently loaded products. In addition, as another solution technique, a method of suctioning air from a sterilizing/deodorizing target space and adsorbing or removing contaminated materials by a filter, or an expensive catalyst that removes offensive odor has been proposed. However, maintenance such as replacement of a filter is necessary for long-term use. In addition, in many cases, unsatisfactory performance may be received because the performance of a filter is insufficient. Even when the filter performance is good, a large and expensive catalyst body and a high maintenance cost are required in many cases.

Recently, air cleaners and air conditioners for generating negative ions or ozone for cleaning and refreshing indoor air have been introduced. There have been proposed a plurality of technologies for deodorizing a target space by using a negative ion/ozone generation device that simultaneously generates negative ions and ozone that have a deodorizing effect.

First, a negative ion/ozone generation device according to Patent Literature 1 is designed to be installed on a ceiling of a room and is configured such that a positive electrode is located beneath a negative electrode. According to this configuration, a downstream airflow containing negative ions and ozone can be generated even without using a fan or a motor.

Next, a negative ion/ozone generation device according to Patent Literature 2 includes a cathode electrode having a needle-shaped tip and a cylindrical ground electrode that is concentrically installed in parallel to the cathode electrode, in which the cathode electrode and the ground electrode are relatively movable. A high voltage is applied to the cathode electrode to adjust the distance between the tip portion of the cathode electrode and the end surface of the ground electrode, thereby generating negative ions or ozone.

Next, a negative ion/ozone generation device according to Patent Literature 3 applies a direct current high voltage between a needle electrode and an earth electrode to cause corona discharge to occur at the apical portion of the needle electrode, thereby generating ozone and negative ions.

Next, a negative ion/ozone generation device according to Patent Literature 4 includes a positive electrode including a metal plate having one or more holes with an erected portion therearound, and a negative electrode having a tip located adjacent to the holes of the positive electrode. With this configuration, a sufficient airflow is generated by discharge. Thus, an air stream capable of diffusing generated negative ions and ozone in a space can be generated even without using a separate blower device such as a fan or a pump.

The inventions according to Patent Literatures 1 to 4 describe generating ions and ozone and applying the same to a target object. However, these technologies, for example, assume that the device is placed in a sterilizing or deodorizing target space, such as inside of a trash can, and performs discharge. For example, if the device is placed in a trash can, an organic matter releasing offensive odor may be resolved by microorganisms to generate flammable gas such as methane gas. When discharge is performed in this state, fire or explosion may occur due to the generation of spark.

Thus, in order to remove such a danger, research is being conducted to develop an external sterilizing/deodorizing device that performs discharge outside a space of a target object, generates ions and ozone, and introduces the generated materials into the space in which the target object is placed (Patent Literature 5).

CITATION LIST

Patent Literature

Patent Literature 1: Japanese Utility Model Registration No. 3100754
Patent Literature 2: JP 2003-342005 A Patent Literature 3: JP 2004-18348 A
Patent Literature 4: JP 2005-13831 A
Patent Literature 5: Japanese Utility Model Registration No. 3155540

SUMMARY OF INVENTION

Technical Problem

The inventions according to Patent Literatures 1 to 5 can generate ions and ozone, but have difficulties in distributing the generated ions over the entirety of the room. More specifically, the wind power of ion wind including the ions and ozone generated using these technologies is low. In order to distribute the ions and ozone over the entirety of the room, additional fan or the like is needed to push forward the ion wind. This addition can achieve the pushing forward of the ion wind, but suffers from dilution of ions included in the ion wind. Furthermore, these technologies provide high ozone concentration near a nozzle. Thus, ozone generated when the device generates ion wind may cause unintentional bleaching of items located adjacent to the device. Use of means for reducing the ozone concentration, such as a filter, has been proposed, but this solution poses another problem such as reduction of a concentration of ions in the ion wind or required replacement of a filter.

The present invention has been made in view of the above circumstances, and thus an objective of the present invention is to provide an ion wind generation device capable of providing a wide range of ion delivery and providing ion wind having a reduced ozone concentration near a nozzle without use of a filter or the like.

Solution to Problem

An ion wind generation device according to an embodiment of the present invention includes an electrode pair including a discharge electrode body having a discharge portion and a counter electrode body having a plurality of end portions, and generates ion wind by corona discharge that occurs due to a potential difference generated between the discharge portion and the end portions. The end portions are located spaced apart from one another in a single plane and disposed around an axis of the discharge electrode body in the single plane or disposed along a line in the single plane.

The end portions are located spaced apart from one another in a single plane. Furthermore, the end portions are disposed around an axis of the discharge electrode body in a plane or disposed along a line. Thus, the discharge electrode body can achieve selective occurrence of discharge between the discharge electrode body and the end portions, and provide ion wind with an adjusted ozone concentration.

Advantageous Effects of Invention

A wide range of ion delivery can be provided and ion wind can be provided with its ozone concentration reduced near a nozzle without use of a filter or the like.

DESCRIPTION OF EMBODIMENTS

Summary of Embodiments of Invention

Figure 1:
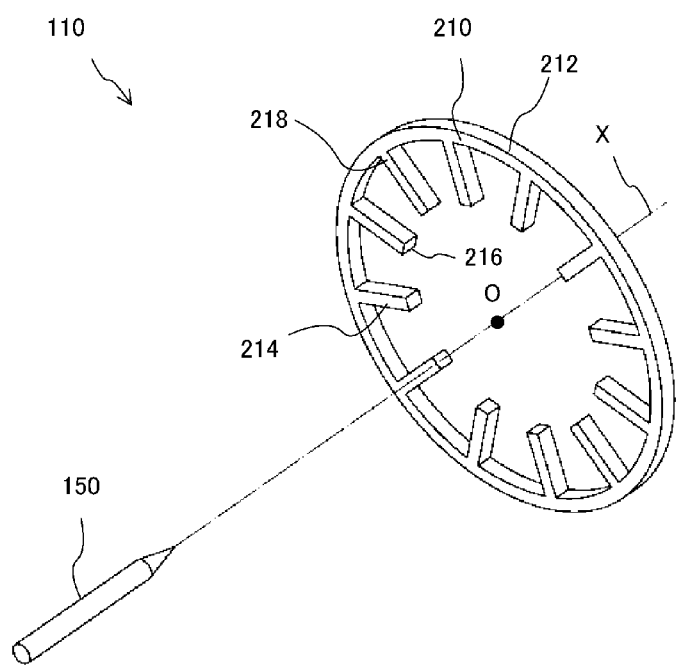
FIG. 1 is a perspective view schematically illustrating an ion wind generation device 110 according to a first embodiment.

According to an embodiment of the present invention, there is provided an ion wind generation device including an electrode pair including a discharge electrode body (for example, discharge electrode bodies 150 to 170 described later) having a discharge portion and a counter electrode body (for example, counter electrode bodies 210 to 510 and 610 to 630 described later) having a plurality of end portions, and generates ion wind by corona discharge that occurs due to a potential difference generated between the discharge portion and the end portions. The end portions (for example, inner end portions 216 described later) are located spaced apart from one another in a single plane and disposed around an axis (for example, an axis X described later) of the discharge electrode body in the single plane.

<<Ion Wind Generation Device>>

The ion wind generation device includes a discharge electrode body and a counter electrode body. The discharge electrode body serves as a discharging electrode and has a discharge portion. The counter electrode body serves as a receiving electrode and has a plurality of end portions.

<Occurrence of Corona Discharge>

A potential difference is generated between the discharge portion of the discharge electrode body and the end portions of the counter electrode body to cause corona discharge to occur, which generates ion wind. Preferably, the potential difference forms an electric field in which the corona discharge is more likely to occur. For example, the electric field in which the corona discharge is more likely to occur can be formed by a relative position or a distance between the discharge portion of the discharge electrode body and the end portions of the counter electrode body, shapes of the discharge portion and the end portions, or the potential difference between the discharge portion and the end portions. This corona discharge generates ozone.

<Discharge Electrode Body>

As described above, the discharge electrode body serves as a discharging electrode and has a discharge portion. The discharge electrode body may have any shape, arrangement, and number as long as the discharge electrode body can define an axis extending along a predetermined direction. For example, when the discharge electrode body has an elongated shape (see FIG. 1 referred to later), the direction of the axis may be a longitudinal direction of the discharge electrode body. When the discharge electrode body has symmetry, the axis of symmetry can be the axis of the discharge electrode body. The symmetry can be axial symmetry, point symmetry, rotational symmetry, or the like. For example, when the discharge electrode body has a disc shape or an annular shape (see FIGS. 23 to 25 referred to later), the axis may be an axis that passes through the center or the center of gravity of the counter electrode body and extends vertically relative to a plane including the disc and the ring.

Furthermore, the axis need not pass through the center or the like of the discharge electrode body. The axis may be shift from the center of the discharge electrode body as long as the axis is associated with features of the contour or arrangement of the discharge electrode body.

Thus, the discharge electrode body may have any shape and arrangement that can define the axis, and is not limited to a particular shape or number.

<Counter Electrode Body>

The counter electrode body has a plurality of end portions. The end portions are disposed in a single plane. The entirety of the counter electrode body need not be disposed in the single plane, and the counter electrode body may be disposed as long as the end portions are included in the single plane. Such an arrangement of the end portions in the single plane causes corona discharge to occur at any of the end portions, which can improve discharge efficiency of the entirety of the counter electrode body.

The end portions may be disposed at any position as long as the end portions are disposed in a single plane, and the overall shape of the counter electrode body can be determined as appropriate. That is, the overall shape of the counter electrode body need not be flat, and the counter electrode body may be shaped to have three-dimensionally recessed and projected portions as long as the end portions are included in the single plane. Furthermore, the discharge electrode body need not be included this plane. The discharge electrode body can be disposed at a position in a plane that is different from the plane where the end portions are included. The overall shape of the discharge electrode body also need not be flat.

The end portions of the counter electrode body are disposed to be spaced apart from one another and disposed around the axis of the discharge electrode body. As described above, the axis of the discharge electrode body may be any axis as long as the axis is associated with the features of the contour or arrangement of the discharge electrode body. Such arrangement of the spaced-apart end portions causes corona discharge to be more likely to selectively occur at the end portions that are spaced apart from one another, which can cause intermittent occurrence of ozone. A concentration of ozone generated by the entirety of the counter electrode body can be reduced.

The end portions may be disposed at any positions as long as the end portions are disposed to be spaced apart around the axis of the discharge electrode body. The end portions need not be disposed along a constant circumference or circular arc. The end portions need not be spaced equally (at the same distance or angle).

When the end portions are disposed along a shape of a circumference having a constant radius, the distances between the discharge electrode body and all the end portions can be the same, corona discharge can be made to occur evenly at all the end portions, and the discharge efficiency of the entirety of the counter electrode body can be improved.

<End Portions and Non-End Portions>

The counter electrode body has a plurality of end portions and non-end portions different from the end portions. The end portions are disposed at more protruded position and closer to the discharge portion of the discharge electrode body than the non-end portions. That is, the end portions and the non-end portions are arranged so that the distance between the end portions and the discharge portion is shorter than the distance between the non-end portions and the discharge portion.

Examples of the end portions include inner end portions 216 described later.

The non-end portions may be any portions of the counter electrode body as long as the non-end portions are different from the end portions thereof. Examples of the non-end portions includes an outer periphery 212 described later and radial portions such as projection members 214 (214a, 214b, 214S, 214L), 274 (274a, 274b), 334, 354, 364, 374 (374a, 374b), 384, 394, 404, 414, 424, 437a, and 477a.

Arrangement of the end portions to be closer to the discharge portion induces more active occurrence of corona discharge at the end portions than the non-end portions. This arrangement forms in the counter electrode body the end portions at which the corona discharge is more likely to occur and the non-end portions at which the corona discharge is less likely to occur. That is, the corona discharge is more likely to occur at the end portions and less likely to occur at the non-end portions. Thus, ozone is also more likely to be generated at the end portions due to the more likely occurrence of the corona discharge. In contrast, ozone is less likely to be generated at the non-end portions due to the less likely occurrence of the corona discharge. The positions at which ozone is more likely to be generated and the positions at which ozone is less likely to be generated can be selectively formed in the discharge electrode body. This formation enables intermittent generation of ozone and variations in the concentration of ozone generated by an entirety of the counter electrode body.

<Proximal Portion and Distal Portion>

As described above, the more likely occurrence of the corona discharge can be controlled based on the distance from the discharge portion of the discharge electrode body. In other words, the discharge electrode body can be configured to set the end portions to be located as proximal portions closer to the discharge portion and set the non-end portions to be located as distal portions farther from the discharge portion than end portions.

<Shapes of End Portions and Non-End Portions>

The more likely occurrence of the corona discharge can be controlled not only based on the distance from the discharge portion of the discharge electrode body, but also based on the shape of the end portions. For example, forming the end portions to have a sharp shape toward the axis enables formation of electric field that causes the corona discharge to be more likely to occur around the end portions, which results in the more likely occurrence of the corona discharge at the end portions. In contrast, forming the non-end portions to have a smooth shape can cause the corona discharge to be less likely to occur at the non-end portions.

<Corona Discharge at the Non-End Portions>

As described above, the non-end portions are disposed at position farther from the discharge electrode body than the end portions. Thus, the corona discharge is less likely to occur at the non-end portions. However, the non-end portions are not without occurrence of the corona discharge. The corona discharge is more likely to occur at portions of the non-end portions near the end portions since the portions are relatively close to the discharge electrode body. This occurrence of the corona discharge at the non-end portions as well can supplement the volume of ion wind and maintain the volume of ion wind generated by the entirety of the discharge electrode body.

For example, when the non-end portions are portions that are gradually farther away from the discharge electrode body (for example, radial portions such as projection members 214 (214*a*, 214*b*, 214S, 214L), 274 (274*a*, 274*b*), 334, 354, 364, 374 (374*a*, 374*b*), 384, 394, 404, 414, 424, 437*a*, and 477*a* described later), the corona discharge is more likely to occur at positions near the end portions, and the corona discharge becomes less likely to occur as the distance between the discharge electrode body and the portions of the non-end portions is larger. Even in such a case, the corona discharge is more likely to occur at the positions near the end portions, which can thus generate ion wind and supplement the volume of the ion wind.

<Arrangement of the Plurality of End Portions Along a Line>

The end portions (for example, inner end portions 616 described later) may be located spaced apart from one another in a single plane and disposed along a line (for example, an imaginary line L described later). When the end portions are disposed spaced apart from one another along a line, the end portions are also disposed at positions near the discharge portion of the discharge electrode body (for example, the discharge electrode bodies 160 and 170 described later), and the non-end portions different from the end portions are also disposed at portions farther from the discharge portion of the discharge electrode body. Such arrangement enables corona discharge to selectively occur at the end portions relative to the non-end portions. This selective occurrence provides intermittent generation of ozone, which can reduce a concentration of ozone generated by the entirety of the counter electrode bodies (for example, counter electrode bodies 610 to 630 described later).

Here again, the entirety of the counter electrode body need not be disposed in the single plane, and the counter electrode body may be disposed as long as the end portions are included in the single plane. Such an arrangement of the end portions in the single plane causes corona discharge to occur at any of the end portions, which can improve discharge efficiency of the entirety of the counter electrode body.

The end portions may also be disposed at any position as long as the end portions are disposed in a single plane, and the overall shape of the counter electrode body can be determined as appropriate. That is, the overall shape of the counter electrode body need not be flat, and the counter electrode body may be shaped to have three-dimensionally recessed and projected portions as long as the end portions are included in the single plane. Furthermore, the discharge electrode body need not be included this plane. The discharge electrode body can be disposed at a position in a plane that is different from the plane where the end portions are included. The overall shape of the discharge electrode body also need not be flat.

<Corona Discharge at the Non-End Portions>

As described above, the non-end portions are disposed at position farther from the discharge electrode body than the end portions. Thus, the corona discharge is less likely to occur at the non-end portions. However, the non-end portions are not without occurrence of the corona discharge. The corona discharge is more likely to occur at portions of the non-end portions near the end portions since the portions are relatively close to the discharge electrode body. This occurrence of the corona discharge at the non-end portions as well can supplement the volume of ion wind and maintain the volume of ion wind generated by the entirety of the discharge electrode body.

For example, when the non-end portions are portions that are gradually farther away from the discharge electrode body (for example, portions in the radial direction such as projection members 614 described later), the corona discharge is more likely to occur at position near the end portions, and the corona discharge is less likely to occur as the distance between the discharge electrode body and the portions of the non-end portions is larger. Even in such a case, the corona discharge is more likely to occur at the positions near the end portions, which can thus generate ion wind and supplement the volume of the ion wind.

<<Description of Ion Wind Generation Device>>

The detailed structure of the ion wind generation device according to the present invention is described hereinafter. The following exemplifications are given merely by way of example. Any embodiment or variation given herein as an example is not to be construed in a limiting sense as being applied to a particular target, and can be any combination. For example, a variation of an embodiment is to be understood as a variation of another embodiment, and even if a variation is described separately from another variation, a combination of both the variations is to be understood as also being described.

The "electrode body" and the "electrode" may be used interchangeably in the specification.

First Embodiment

As illustrated in FIG. 1, an ion wind generation device 110 according to the first embodiment includes an electrode pair of a discharge electrode body 150 and any of counter electrode bodies 210 to 510. The discharge electrode body 150 and any of the counter electrode bodies 210 to 510 include an electrical conductor such as metal. The ion wind generation device 110 of the first embodiment can selectively include any one of the counter electrode bodies 210 to 510. Each of the counter electrode bodies 210 to 510 has the corresponding shape illustrated in FIGS. 2 to 18.

The principle of the ion generation of the ion wind generation device 110 of the first embodiment is similar to that of the existing ion wind generation device. That is, a potential difference is generated between the discharge electrode body 150 and the counter electrode body 210 to 510 causes corona discharge to occur between these electrodes. During corona discharge, ions released from the discharge electrode body 150 migrate toward the counter electrode body 210 to 510. Repeated collisions of ions with air molecules during the migration form the air stream including ions directing from the discharge electrode body 150 toward the counter electrode body 210 to 510. This air stream is ion wind.

In this embodiment, as illustrated in FIGS. 2 to 18, the counter electrode bodies 210 to 510 are particular structures of the counter electrode bodies. A frequency or distribution of occurrence of the corona discharge is controlled, and a flow of air generated by the corona discharge is controlled, thereby reducing a concentration of ozone included in the ion wind while ensuring a volume of ion wind.

Specific structures of the counter electrode bodies 210 to 510 and the discharge electrode body 150 of the present invention are described hereinafter.

The ion wind generation device 110 of the first embodiment can selectively include any one of the counter electrode bodies 210 to 510. Here, the description is made using the counter electrode body 210 representatively.

The entire contour of the counter electrode body 210 of the present invention has a generally annular or circular shape. The counter electrode body 210 has a plurality of projection members 214. Each of the projection members 214 has an inner end portion 216 located closest to the center of the ring of the counter electrode body 210. Thus, the counter electrode body 210 has a plurality of the inner end portions 216 located spaced apart from one another in a single plane and disposed around an axis X of the discharge electrode body 150 in the single plane. The counter electrode body 210 of the present invention is formed by an electrical conductor such as metal.

The counter electrode body 210 has an annular outer periphery 212. In this embodiment, the annular shape may be any shape as long as the shape is circular and also the contour of the annular shape can be defined by only a curve, lines, curves, a combination of lines and curves, or the like. The counter electrode body 210 has a plurality of projection members 214. The projection members 214 are provided at the outer periphery 212 of the counter electrode body 210 and extend toward the center O of the counter electrode body 210. In this embodiment, the center O of the counter electrode body 210 is located on the axis X of the discharge electrode body 150 and included in the axis X of the discharge electrode 150.

Each of the projection members 214 is electrically connected to the outer periphery 212 and is configured to be equipotential. The electrical connection of any of the projection members 214 to the outer periphery 212 may be sufficient. The specific examples of the counter electrode bodies 210 to 510 are described hereinafter.

<<First Type of Counter Electrode Body>>

FIGS. 2 to 5 are front views illustrating a first type of counter electrode bodies 210 to 260. The projection members 214 of the first type of counter electrode bodies 210 to 260 have a single linear shape.

Figure 2:
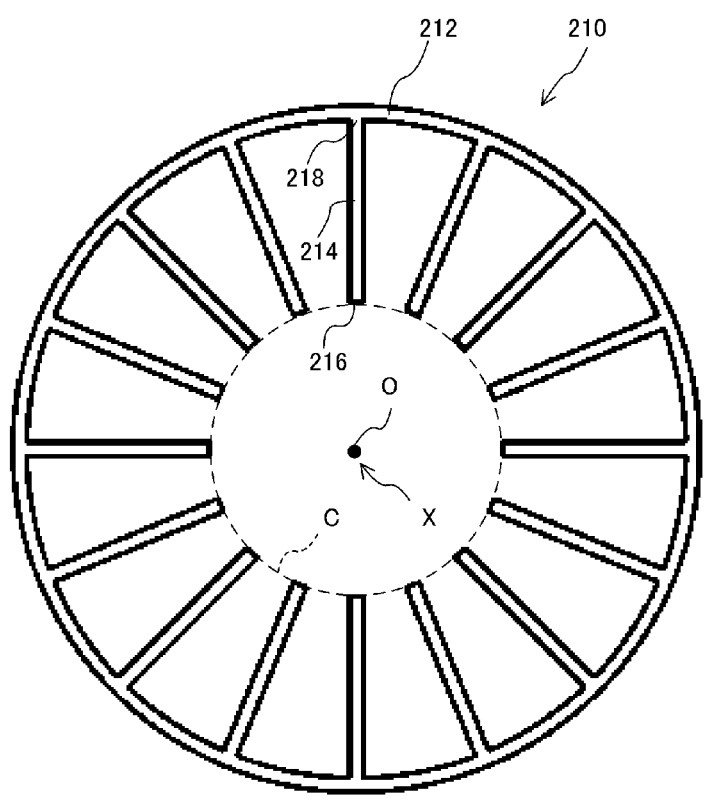
FIG. 2 is a front view illustrating a structure of a counter electrode body 210.

As illustrated in FIG. 2, the counter electrode body 210 has the ring-shaped outer periphery 212. In this embodiment, an annular shape or a ring shape refers to a loop shape and a shape of region surrounded by two concentric circles having different radii. For example, the counter electrode body 210 illustrated in FIG. 2 has sixteen projection members 214 formed in a radial or diametric direction of the counter electrode body 210. Each of the sixteen projection members 214 has a longitudinal length having the same length, and has a linear shape. The "linear" shape here is a shape of straight line. The projection members 214 have outer end portions 218 located closest to the outer periphery 212 of the counter electrode body 210. The outer end portions 218 are disposed (evenly) spaced equiangularly along the outer periphery 212. Not all the outer end portions 218 need to be electrically connected to the outer periphery 212. A part of the outer end portions 218 may be electrically connected to the outer periphery 212 to be equipotential to the outer periphery 212.

The projection members 214 are disposed such that the inner end portions 216 are spaced apart from one another and located in the same plane. Imaginary smooth connection of two adjacent inner end portions 216 from one after another forms an imaginary circle C at a central portion of the counter electrode body 210 in the same plane as that of the counter electrode body 210.

The inner end portions 216 are disposed around the axis X of the discharge electrode body 150 in the same plane as that of the counter electrode body 210. In other words, the arrangement is such that the axis X of the discharge electrode body 150 is perpendicular to the plane in which the imaginary circle C of the counter electrode body 210 extends. The distance between the center of the imaginary circle C and each of the sixteen inner end portions 216 is uniform. Such arrangement causes corona discharge to intermittently (selectively) occur between the discharge electrode body 150 and each of the sixteen inner end portions 216 when the discharge occurs from the discharge electrode body 150 to the counter electrode body 210, and ion wind generated by the corona discharge is provided along the axis X.

Selective occurrence of the corona discharge between the discharge electrode body 150 and the sixteen inner end portions 216 causes ozone to be intermittently generate to reduce a volume of the generated ozone, thereby reduce a concentration of ozone as a whole.

The sharper shape of the inner end portions 216 can induce formation of an electric field in which the corona discharge is more likely to occur, and provide a more volume of ion wind occurring at the inner end portions 216. In other words, the sharper the shape of the inner end portions 216 are, the more the corona discharge is like to occur compared with the inner end portions 216 having a flat shape.

Figure 8A:
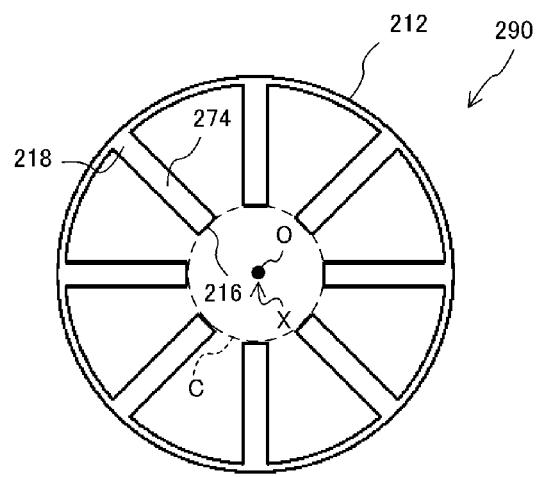
FIG. 8 is a front view illustrating structures of counter electrode bodies 290 and 300.
Figure 8B:
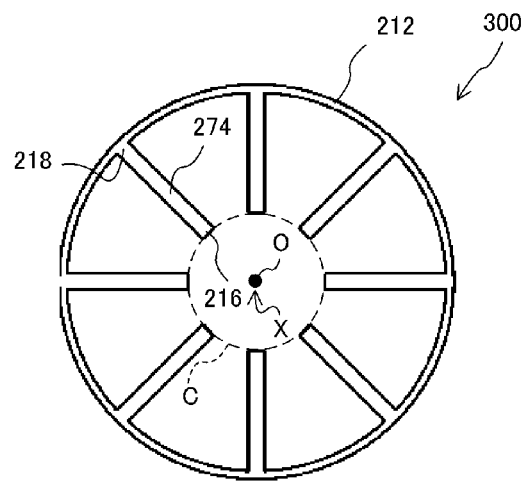

Here, the number of the inner end portions 216 is not particularly limited, and can be changed as appropriate depending on the application or the like. For example, as illustrated in FIGS. 8A and 8B, the counter electrode bodies 290 and 300 having eight projection members 214 can be employed. That is, when the counter electrode bodies 210, 290, and 300 are used having multiple linear projection members 214 as illustrated in FIGS. 2, 8A, and 8B, the number of the linear projection members 214 is not particularly limited.

Preferably, two or more linear projection members 214 are provided to cause the corona discharge to be more likely to occur. Preferably, three or more projection members 214 are provided to form an imaginary circle C by imaginary smooth connection of the inner end portions 216. As another feature, the distance between the center of the imaginary circle C and the inner end portions 216, that is, the radius of the imaginary circle C, is smaller than half the radius of the outer periphery 212. The smaller radius of the imaginary circle C causes the corona discharge to be more likely to occur, which can generate a more volume of ion wind. Thus the longitudinal length of the projection members 214 is not particularly limited as long as the length is greater than or equal to half the radius of the outer periphery 212. The number of the projection members 214 can also be changed as appropriate depending on the application. The length of the radius of the outer periphery 212 is not particularly limited.

Figure 3:
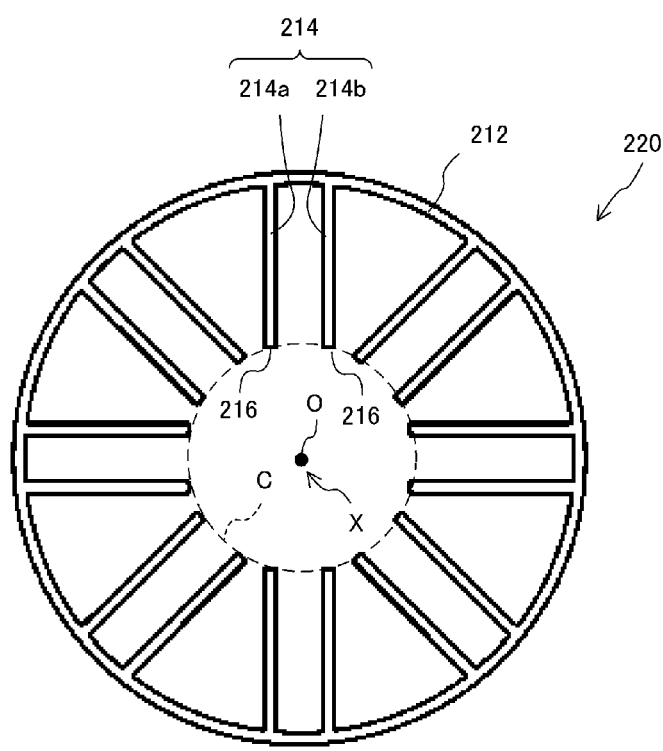
FIG. 3 is a front view illustrating a structure of a counter electrode body 220.

As illustrated in FIG. 3, the projection members 214 need not be disposed (evenly) spaced equiangularly along the outer periphery 212. The counter electrode body 220 illustrated in FIG. 3 has pairs of two projection members 214a and 214b, and the pairs are disposed along the outer periphery 212 such that the paired two projection members 214a and 214b are parallel to each other. Eight sets of projection members that includes the pairs of two projection members 214a and 214b are disposed (evenly) spaced equiangularly in the outer periphery 212. Thus the counter electrode body 220 illustrated in FIG. 3 has a total of sixteen projection members 214.

The counter electrode body 220 illustrated in FIG. 3 sets the two projection members 214a and 214b to one set of projection members, but the combination is not particularly limited thereto. The one set of projection members may include three projection members 214a, 214b, and 214c or four or more projection members. The number of sets of projection members is also particularly limited. Furthermore, arrangement may be such that only a part of the projection members 214 forms the sets of projection members, and the other remaining part of the projection members 214 does not form the sets of projection members. Thus even if the projection members 214 are not disposed (evenly) spaced equiangularly along the outer periphery 212, the imaginary circle C can be formed by combination of the inner end portions 216 of the projection members 214 having the same longitudinal length.

FIGS. 2 and 3 described above illustrate examples in which all the inner end portions 216 of the projection members 214 are disposed spaced equiangularly around the axis X of the discharge electrode body 150, but the arrangement is not limited thereto. For example, the counter electrode body 230 illustrated in FIG. 4 has eight projection members 214 disposed therein. Four projection members 214L of the eight projection members 214 have the same longitudinal length, and the remaining four projection members 214S have a longitudinal direction that is shorter than that of the projection members 214L. Such arrangement also forms an imaginary circle C by the inner end portions 216 of the four long projection members 214L.

Figure 4:
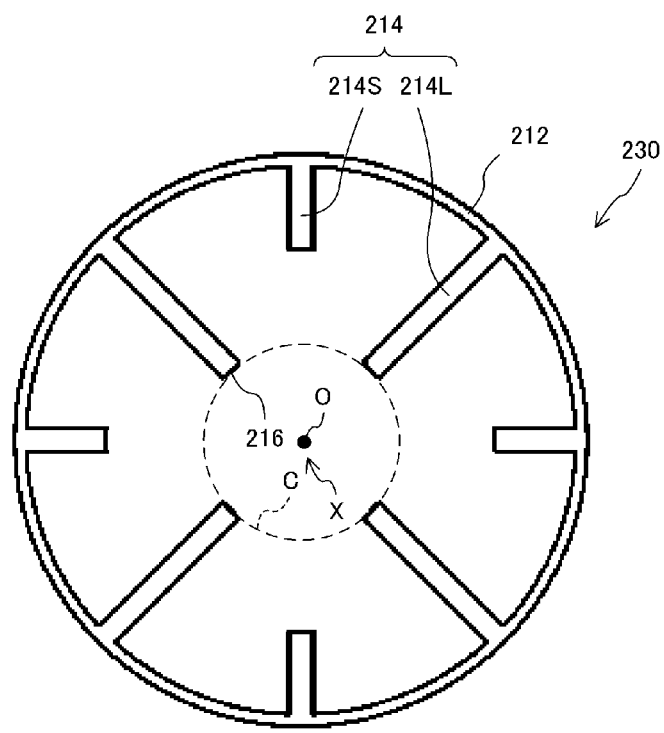
FIG. 4 is a front view illustrating a structure of a counter electrode body 230.
Figure 5A:
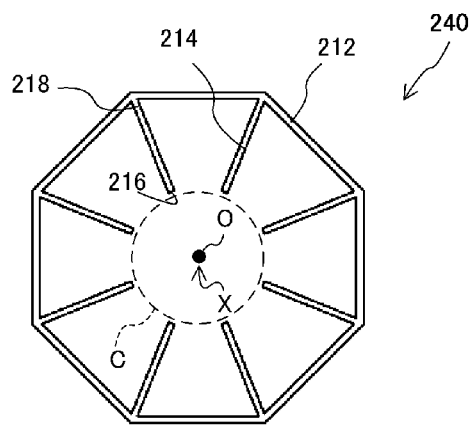
FIG. 5 is a front view illustrating structures of counter electrode bodies 240, 250, and 260.
Figure 5B:
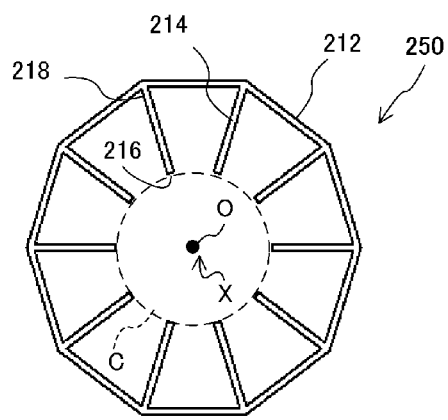
Figure 5C:
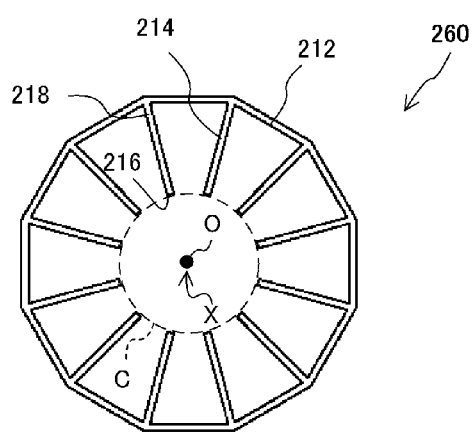

In FIGS. 2 to 4, the shape of the outer peripheries 212 of the counter electrode bodies 210, 220, and 230 is a ring shape, but is not limited thereto. For example, the contour of the counter electrode body 240 can be octagonal as illustrated in FIG. 5A, the contour of the counter electrode body 250 can be decagonal as illustrated in FIG. 5B, and the contour of the outer electrode 260 can be dodecagonal as illustrated in FIG. 5C. The shape of the outer periphery 212 can be various types of annular polygonal shape. In the examples illustrated in FIGS. 5A, 5B, and 5C, the projection members 214 are disposed so as to extend from the vertices of the polygon toward the center, but the arrangement is not limited thereto. The projection members 214 may be disposed so as to extend from the sides of the polygon toward the center.

<<Second Type of Counter Electrode Body>>

The above-described first type of counter electrode bodies 210 to 260 illustrated in FIGS. 2 to 5 are the examples in which the counter electrode bodies have the projection members 214 having a linear shape. The shape of the projection members 214 is not limited to the linear shape, and may have another shape as long as the projection members 214 are equipotential with the outer periphery 212 and have the inner end portions 216. Examples of the other shapes are described hereinafter.

Figure 6:
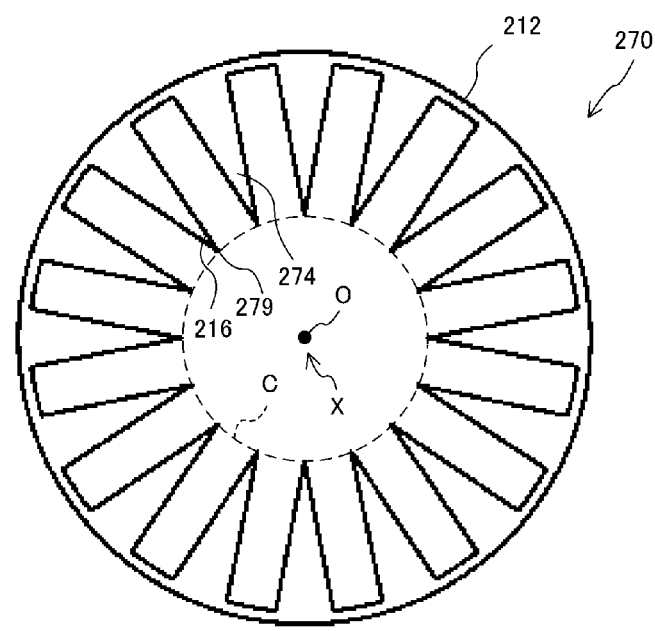
FIG. 6 is a front view illustrating a structure of a counter electrode body 270.

The counter electrode body 270 illustrated in FIG. 6 is provided with a plurality of plate-like projection members 274. Each of the plate-like projection members 274 extends toward the center O (axis X) of the outer periphery 212 having a ring shape. In an example illustrated in FIG. 6, the counter electrode body 270 has sixteen projection members 274, and each of the projection members 274 has a plate-like fan shape.

Similarly to the projection members 214 having a linear shape the inner end portions 216 extend from the outer periphery 212 toward the center C (axis X) of the counter electrode body 270. Imaginary smooth connection of vertices 279 of the inner end portions 216 forms an imaginary circle C.

The vertices 279 of the inner end portions 216 are formed to have an acute angle. The electric field in which the corona discharge is more likely to occur between the discharge electrode body 150 and the vertices 279 can be formed. The sixteen projection members 274 are disposed (evenly) spaced equiangularly along the outer periphery 212, and spaced apart from one another along the outer periphery 212.

Figure 7:
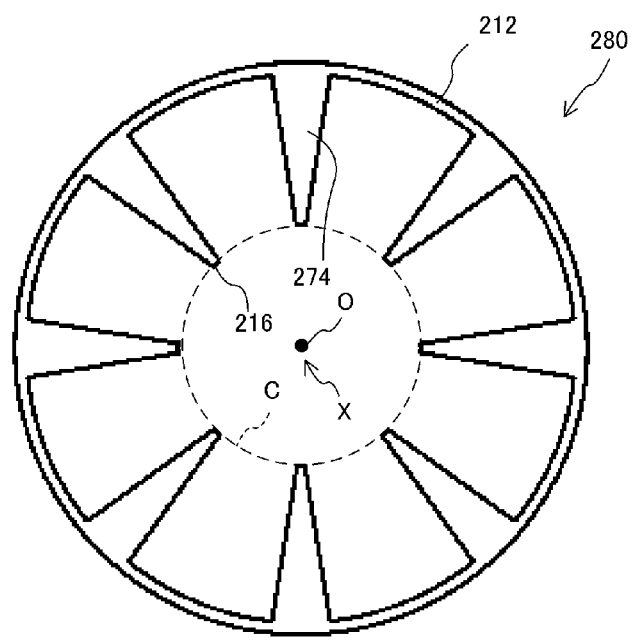
FIG. 7 is a front view illustrating a structure of a counter electrode body 280.

The number of the projection members 274 of the counter electrode body 270 can be changed without any problem, and the shape of the inner end portions 216 can be changed without any problem. For example, the counter electrode body 280 illustrated in FIG. 7 has eight projection members 274 and has the inner end portions 216 not formed to have an acute angle. That is, the projection members 274 illustrated in FIG. 7 is a fan-shaped projection members 274 whose portion near the vertex of the fan shape is cut out along a line. When the inner end portions 216 as illustrated in FIG. 7 have a shape not having an acute angle, imaginary smooth connection of the inner end portions 216 of the projection members 274 to include two angles of the inner end portions 216 forms an imaginary circle C included in the same plane as that of the counter electrode body 280 at the center of the counter electrode body 280.

The shape of the plate-like projection members 274 may be changed. For example, the projection members 274 may have a rectangular shape, as illustrated as the counter electrode body 290 in FIG. 8A and as the counter electrode body 300 in FIG. 8B. The transverse length of the projection members 274, that is, the thickness or the width, can be changed as appropriate. The projection members 274 of the counter electrode body 290 have a thickness greater than that of the projection members 274 of the counter electrode body 300.

Figure 9:
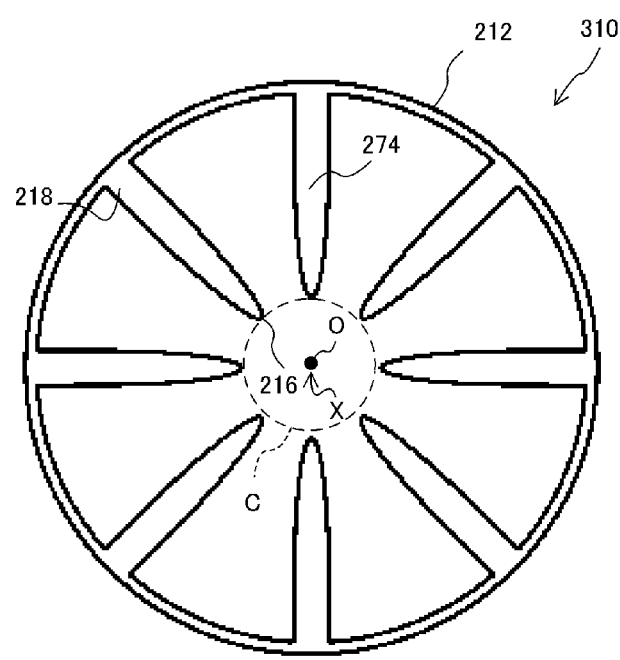
FIG. 9 is a front view illustrating a structure of a counter electrode body 310.

As illustrated in FIG. 9, the projection members 274 may be shaped such that the inner end portions 216 are gradually thinner from the outer periphery 212 toward the center C (axis X) of the counter electrode body 310 and the inner end portions 216 have a distal end portion without edges. In particular, as illustrated in FIG. 9, the distal-most end portions of the inner end portions 216 are formed to be curved and rounded.

Figure 10:
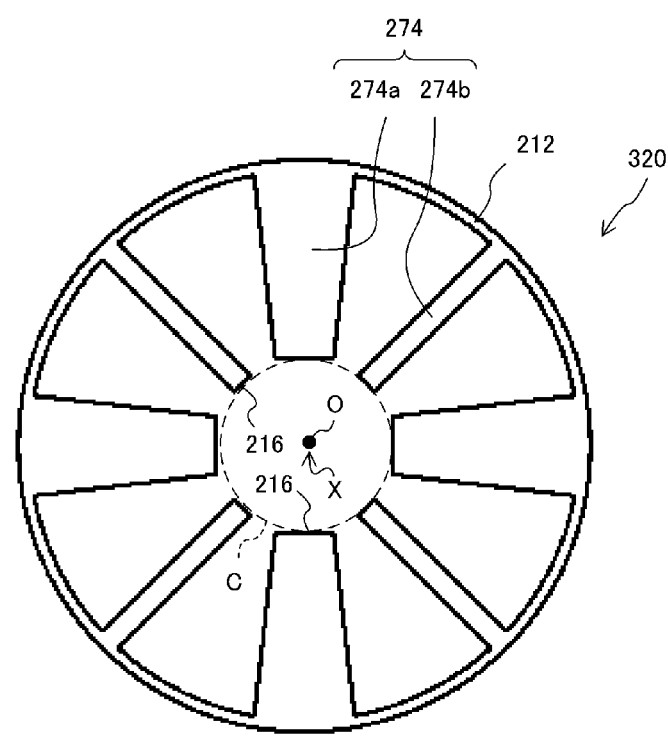
FIG. 10 is a front view illustrating a structure of a counter electrode body 320.

Furthermore, as illustrated in FIG. 10, the shapes of the projection members 274 may be a combination of projection members 274a having a linear shape and projection members 274b having a plate-like shape. With such arrangement, imaginary smooth connection of the edges of the end portions of the projection members 274 also forms an imaginary circle C in the same plane as that of the counter electrode body 320 at the central portion of the counter electrode body 320.

Figure 11:
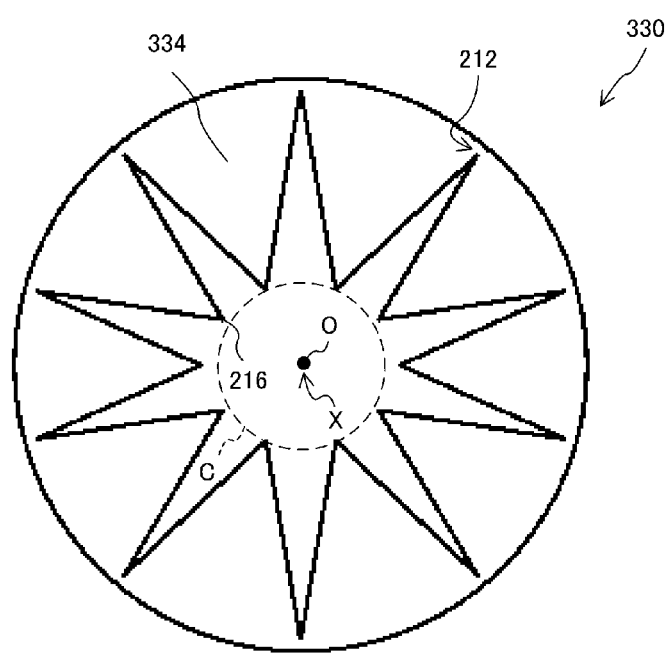
FIG. 11 is a front view illustrating a structure of a counter electrode body 330.

The above-described examples show that the adjoining projection members 214 and the adjoining projection members 274 are disposed spaced apart from one another. As in the counter electrode body 330 illustrated in FIG. 11, portions of adjoining projection members 334 may be formed to be connected to one another. For example, as illustrated in FIG. 11, the projection members 334 having a fan shape may be configured to be disposed adjacent to one another at the outer periphery 212. In such a case, again, smooth connection of the adjacent inner end portions 216 forms an imaginary circle C in the same plane as that of the counter electrode body 330 at the central portion of the counter electrode body 330.

Figure 12:
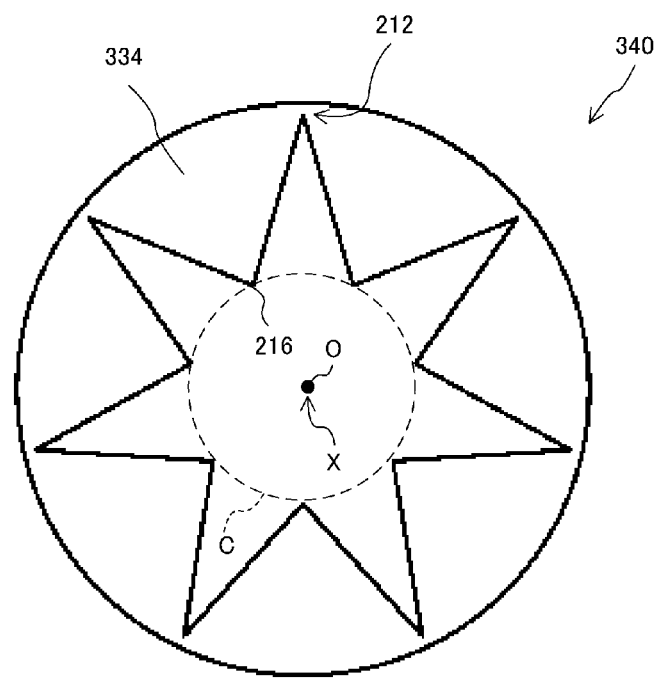
FIG. 12 is front view illustrating a structure of a counter electrode body 340.

Furthermore, as in the counter electrode body 340 illustrated in FIG. 12, the number or shape of the projection members 334 may be changed. For example, as illustrated in FIG. 12, the number of the plate-like projection members may be increased compared with that of the counter electrode bodies 330 in FIG. 11. With a more number of the inner end portions 216 provided, the shape of space formed by imaginary connection of the vertices of the inner end portions 216 in a curve can be closer to a circle (imaginary circle C).

In this second type of counter electrode bodies, when corona discharge occurs between the discharge electrode body 150 and the inner end portions 216 of the counter electrode bodies 270 to 340, the ion wind generated at the inner end portions 216 of the counter electrode bodies 270 to 340 is released toward sides of the counter electrode bodies 270 to 340 on which the counter electrode bodies 270 to 340 do not face the discharge electrode body 150, and negative pressure is generated on the sides of the counter electrode bodies 270 to 340 on which the counter electrode bodies 270 to 340 do not face the discharge electrode body 150. Air surrounding the counter electrode bodies 270 to 340 is drawn toward the space in which the negative pressure is generated, and the drawn air forces the ion wind toward the sides in which the counter electrode bodies 270 to 340 do not face the discharge electrode body 150, thereby enabling an increase of power of the ion wind.

Similarly to the first type of counter electrodes, this second type of counter electrode bodies is also characterized in that the radius of the imaginary circle C is smaller than half the radius of the outer periphery 212. The shapes of the projection members 274 (including 274a and 274b) and the projection members 334 may be changed as appropriate as long as the radial lengths of the projection members 274 (including 274a and 274b) and the projection members 334 in the corresponding counter electrode bodies 270 to 340 are at least half the radius of the outer periphery 212.

<<Third Type of Counter Electrode Body>>

The above-described examples of the counter electrode bodies 210 to 260 illustrated in FIGS. 2 to 5 show that a single linear projection member 214 is provided. In contrast, the counter electrode body may use projection members formed by connecting multiple linear members. The counter electrode body may have projection members each formed such that the multiple linear members are connected to form a space that is surrounded by the multiple linear members and that appears as if the plate-like projection member is bored at the inner portion thereof, as illustrated in FIGS. 13 and 14.

The shape of such formed projection member is hereinafter referred to as a bored plate-like shape. The projection members can be shaped like the projection members of the counter electrode bodies 350 to 380 as illustrated in FIGS. 13A to 13D.

Figure 13A:
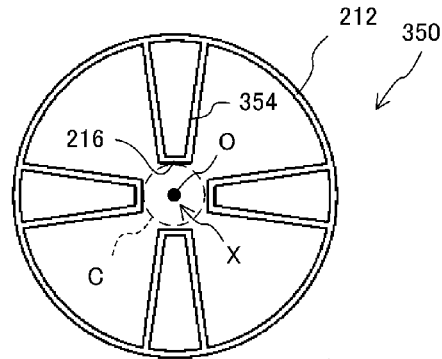
FIG. 13 is a front view illustrating structures of counter electrode bodies 350, 360, 370, and 380.

The projection members 354 of the counter electrode body 350 illustrated in FIG. 13A have a substantially trapezoidal profile, and can be formed by boring a substantially trapezoidal plate or by combining three linear members. Four projection members 354 are disposed spaced 90 degrees in the outer periphery 212.

Figure 13B:
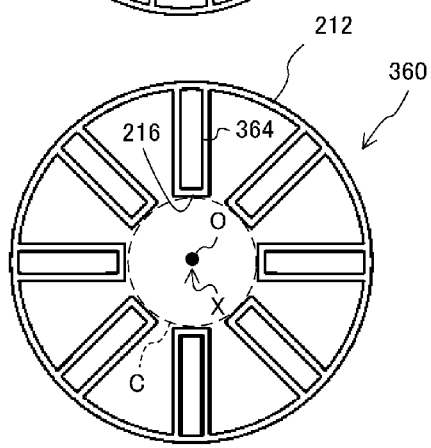

The projection members 364 of the counter electrode body 360 illustrated in FIG. 13B have a substantially rectangular profile, and can be formed by boring a substantially rectangular plate or by combining three linear members. Eight projection members 364 are disposed spaced at 45 degree intervals in the outer periphery 212.

Figure 13C:
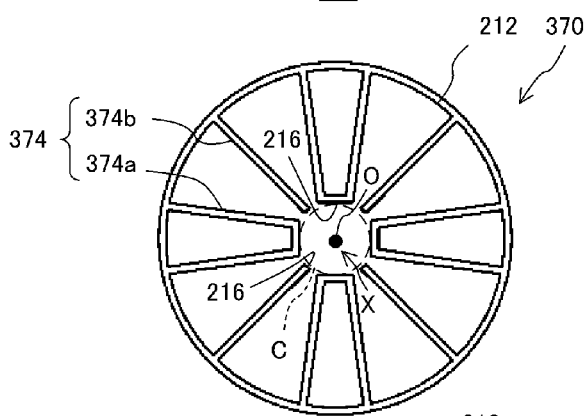

Each projection member 374 of the counter electrode body 370 illustrated in FIG. 13C includes a projection member 374a having a substantially trapezoidal profile and a linear projection member 374b. Four projection members 374a and four projection members 374b are alternately disposed in the outer periphery 212. The substantially trapezoidal projection members 374a can be formed by boring a substantially trapezoidal plate or by combining three linear members. Eight projection members 374 are disposed spaced at 45 degree intervals in the outer periphery 212.

Figure 13D:
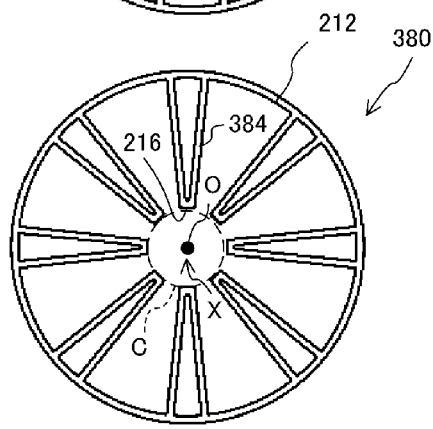

The projection members 384 of the counter electrode body 380 illustrated in FIG. 13D have a substantially trapezoidal profile, and can be formed by boring a substantially trapezoidal plate or by combining three linear members. Eight projection members 384 are disposed spaced at 45 degree intervals in the outer periphery 212.

Imaginary smooth connection of the inner end portions 216 of the projection members of the counter electrode bodies 350 to 380 illustrated in FIGS. 13A to 13D can form an imaginary circle C.

That is, the profiles of the bored plate-like projection members may be a fan shape with the vertex linearly cut or a rectangular shape. The profiles of the board plate-like projection members can be a combination of lines, a combination of curves, or a combination of a line and a curve. The counter electrode bodies may have a combination of a linear projection member and a bored plate-like member.

Furthermore, the counter electrode bodies may have a plurality of projection members having shapes obtained by boring the inner portion of the fan-shaped projection members as illustrated in FIGS. 11 and 12. For example, the projection members can be shaped like the projection members of the counter electrode bodies 390 to 420 as illustrated in FIGS. 14A to 14D. In any case, the projection members have a substantially fan-shaped profile by connection of the adjoining linear members.

Figure 14A:
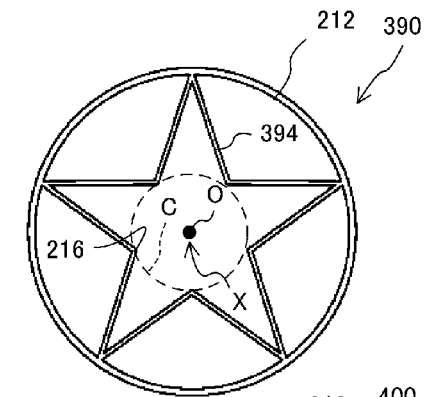
FIG. 14 is a front view illustrating structures of counter electrode bodies 390, 400, 410, and 420.

The counter electrode body 390 illustrated in FIG. 14A has five projection members 394, and the projection members 394 have a substantially fan-shaped profile by connection of the adjoining linear members.

Figure 14B:
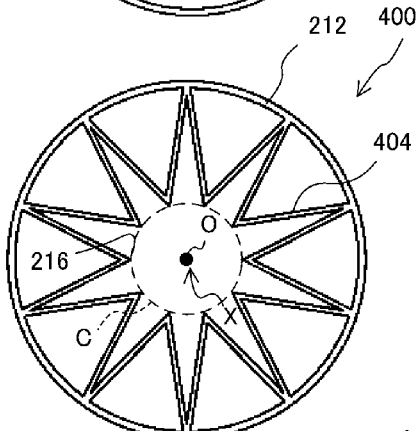

The counter electrode body 400 illustrated in FIG. 14B has ten projection members 404, and the projection members 404 have a substantially fan-shaped profile by connection of the adjoining linear members.

Figure 14C:
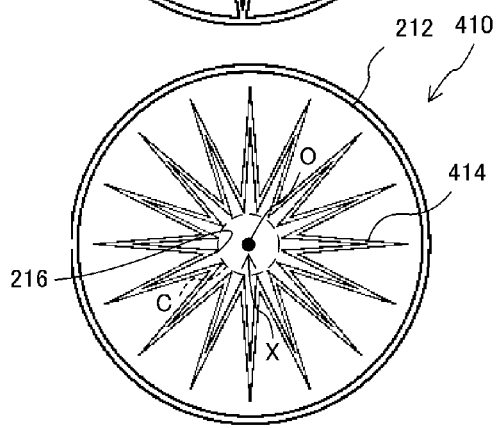

The counter electrode body 410 illustrated in FIG. 14C has sixteen projection members 414, and the projection members 414 have a substantially fan-shaped profile by connection of the adjoining linear members.

Figure 14D:
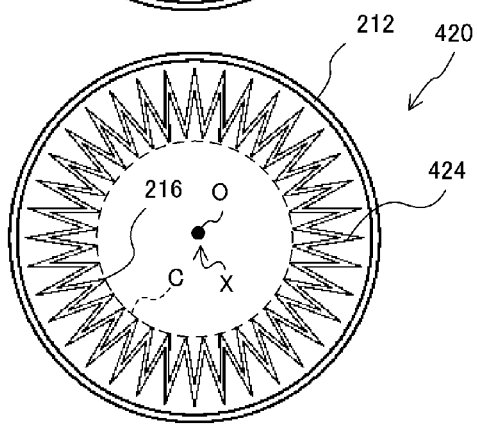

The counter electrode body 420 illustrated in FIG. 14D has thirty-six projection members 424, and the projection members 424 have a substantially fan-shaped profile by connection of the adjoining linear members.

Imaginary smooth connection of the inner end portions 216 of the projection members of the counter electrode bodies 390 to 420 illustrated in FIGS. 14A to 14D can form an imaginary circle C.

Similarly to the first type of counter electrode bodies, this third type of counter electrode bodies is also characterized in that the radius of the imaginary circle C is smaller than half the radius of the outer periphery 212. The shapes of the projection members 354 to 424 may be changed as appropriate as long as the radial lengths of the projection members 354 to 424 in the corresponding counter electrode bodies 350 to 420 are at least half the radius of the outer periphery 212.

<<Fourth Type of Counter Electrode Body>>

Figure 15:
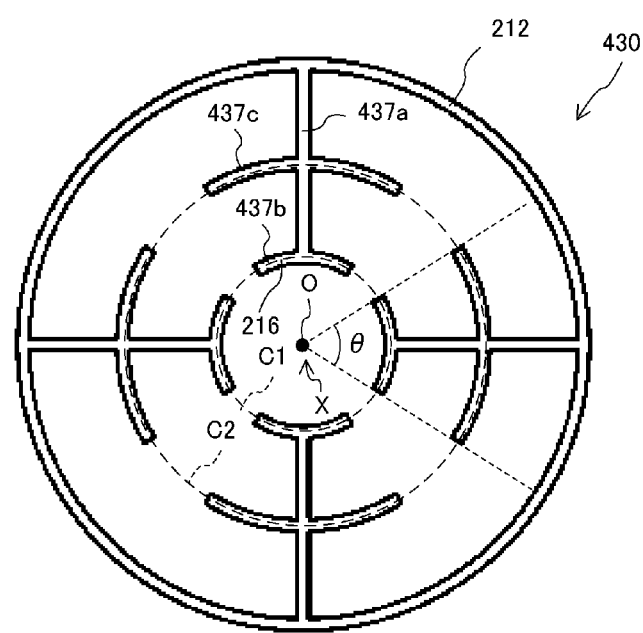
FIG. 15 is a front view illustrating a structure of a counter electrode body 430.

As illustrated in FIG. 15, the counter electrode body 430 has four projection members 437 disposed spaced 90 degrees circumferentially. Each projection members 437 has a linear member 437a, an inner arcuate member 437b, and outer arcuate member 437c. The linear member 437a has a linear shape and is disposed along a radial direction. The inner arcuate member 437b has an arcuate shape and is disposed at an inner end portion 216 of the linear member 437a. The outer arcuate member 437c has an arcuate shape and is disposed substantially at the middle of the linear member 437a.

The inner arcuate members 437b of the respective four projection members 437 are disposed spaced apart 90 degrees from one after another. Connection of the four inner arcuate members 437b can form an imaginary circle C1 in the same plane as the counter electrode body 430. Similarly, the four outer arcuate members 437c are disposed spaced at 90 degree intervals from one after another. Connection of the four outer arcuate members 437c can form an imaginary circle C2 in the same plane as the counter electrode body 430. The diameter of the imaginary circle C2 formed by the outer arcuate members 437c is longer than the diameter of the imaginary circle C1 formed by the inner arcuate members 437b. The imaginary circles C1 and C2 are disposed concentrically with each other.

The inner arcuate members 437b and the outer arcuate member 437c are formed to have the same plane angle θ centered at the center O. That is, the arc-direction length of the outer arcuate members 437c is longer than the arc-direction length of the inner arcuate members 437b.

In the counter electrode body 430 illustrated in FIG. 15, each of the four inner arcuate members 437b is located closest to the discharge electrode body 150 (see FIG. 1) and thus the corona discharge is most likely to occur at the inner arcuate members 437b. In contrast, each of the four outer arcuate members 437c is located farther from the discharge electrode body 150 than the four inner arcuate members 437b and thus the corona discharge is less likely to occur at the outer arcuate members 437c. However, since the arc-direction length of the outer arcuate members 437c is longer than that of the arc-direction length of the inner arcuate members 437b, the corona discharge can be made to more likely to occur at any of the arcuate members.

Selective occurrence of the corona discharge at the four inner arcuate members 437b intermittently generates ozone. In addition, occurrence of the corona discharge at the four outer arcuate members 437c can supplement the volume of ion wind and thus maintain the volume of ion wind generated by the entity of the counter electrode body 430.

Figure 16A:
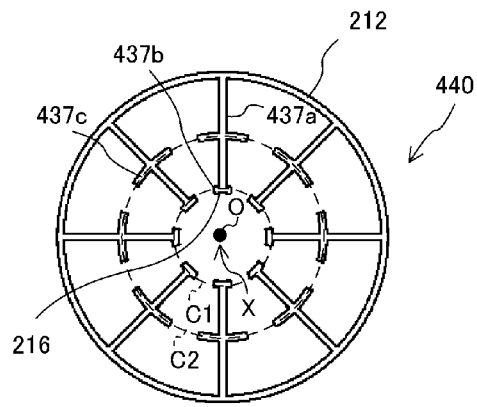
FIG. 16 is a front view illustrating structures of counter electrode bodies 440, 450, and 460.

The counter electrode body 440 illustrated in FIG. 16A has eight projection members 437 disposed spaced at 45 degree intervals circumferentially. Here again, selective occurrence of the corona discharge at the eight inner arcuate members 437b intermittently generates ozone. In addition, occurrence of the corona discharge at the eight outer arcuate members 437c can supplement the volume of ion wind and thus maintain the volume of ion wind generated by the entity of the counter electrode body 440.

Figure 16B:
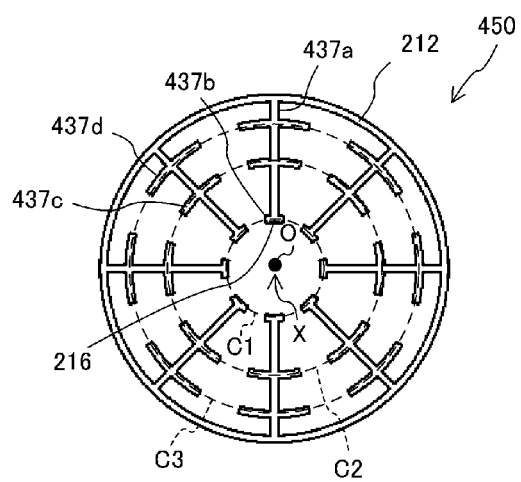

The counter electrode body 450 illustrated in FIG. 16B has eight projection members 437 disposed spaced at 45 degree intervals circumferentially. Each projection members 437 has a linear member 437a, an inner arcuate member 437b, a first outer arcuate member 437c, and a second outer arcuate member 437d.

The eight inner arcuate members 437b are disposed spaced at 45 degree intervals from one after another. Connection of the eight inner arcuate members 437b can form an imaginary circle C1 in the same plane as the counter electrode body 450.

The eight first outer arcuate members 437c are disposed spaced at 45 degree intervals from one after another. Connection of the eight first outer arcuate members 437c can form an imaginary circle C2 in the same plane as the counter electrode body 450.

The eight second outer arcuate members 437d are disposed spaced at 45 degree intervals from one after another. Connection of the eight second outer arcuate members 437d can form an imaginary circle C3 in the same plane as the counter electrode body 450.

Here again, selective occurrence of the corona discharge at the eight inner arcuate members 437b intermittently generates ozone. In addition, occurrence of the corona discharge at the eight first outer arcuate members 437c and the eight second outer arcuate members 437d can further supplement the volume of ion wind and thus maintain the volume of ion wind generated by the entity of the counter electrode body 450.

The diameter of the imaginary circle C2 formed by the first outer arcuate members 437c is longer than the diameter of the imaginary circle C1 formed by the inner arcuate members 437b. The diameter of the imaginary circle C3 formed by the second outer arcuate members 437d is longer than the diameter of the imaginary circle C2 formed by the first outer arcuate members 437c. The imaginary circles C1, C2, and C3 are disposed concentrically with one another.

Figure 16C:
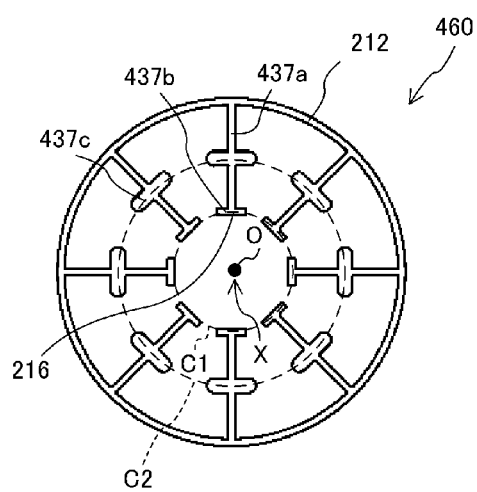

As in the counter electrode body 460 illustrated in FIG. 16C, the shape of the arcuate members 437b may be linear and made wider.

Selective occurrence of the corona discharge at the four inner arcuate members 437b intermittently generates ozone. In addition, occurrence of the corona discharge at the four outer arcuate members 437c can supplement the volume of ion wind and thus maintain the volume of ion wind generated by the entity of the discharge electrode body.

Figure 17A:
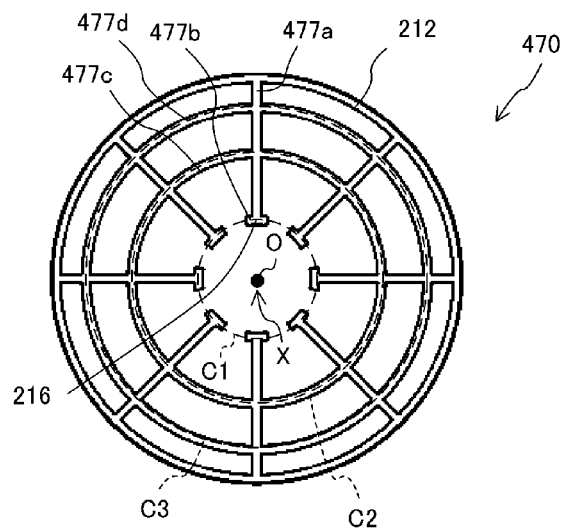
FIG. 17 is a front view illustrating structures of counter electrode bodies 470 and 480.

The counter electrode body 470 illustrated in FIG. 17A has eight projection members 477 disposed spaced 90 degrees circumferentially. Each projection members 477 has a linear member 477a, an inner arcuate member 477b, a first outer annular member 477c, and a second outer annular member 477d.

The linear member 477a has a linear shape and is disposed along a radial direction. The inner arcuate member 477b has an arcuate shape and is disposed at an inner end portion 216 of the linear member 477a.

The first outer annular member 477c and the second outer annular member 477d have an annular shape. Use of the first outer annular members 477c can form an imaginary circle C2 in the same plane as the counter electrode body 430. Use of the second outer annular members 477d can form an imaginary circle C3 in the same plane as the counter electrode body 470.

Here again, selective occurrence of the corona discharge at the eight inner arcuate members 437b intermittently generates ozone. In addition, occurrence of the corona discharge at any of the first outer annular members 477c and the second outer annular members 477d can further supplement the volume of ion wind and thus maintain the volume of ion wind generated by the entirety of the counter electrode body 470.

The diameter of the imaginary circle C2 formed by the first outer annular members 477c is longer than the diameter of the imaginary circle C1 formed by the inner arcuate members 437b. The diameter of the imaginary circle C3 formed by the second outer annular members 477d is longer than the diameter of the imaginary circle C2 formed by the first outer annular members 477c. The imaginary circles C1, C2, and C3 are disposed concentrically with one another.

Figure 17B:
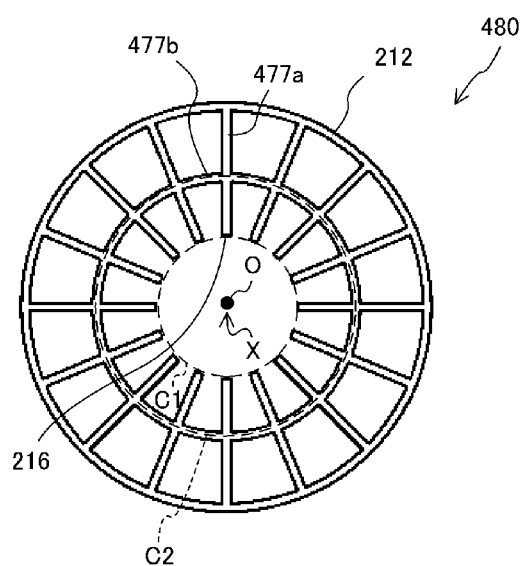

The counter electrode body 480 illustrated in FIG. 17B has sixteen projection members 477 disposed spaced 22.5 degrees circumferentially. Each projection member 477 has a linear member 477a and an annular member 477b.

The linear member 477a has a linear shape and is disposed along a radial direction. The linear member 477a has the inner end portion 216. The annular member 477b has an annular shape.

Use of the inner end portions 216 of the linear members 477a can form an imaginary circle C1 in the same plane as the counter electrode body 480. Use of the annular members 477b can form an imaginary circle C2 in the same plane as the counter electrode body 480.

Here again, selective occurrence of the corona discharge at the sixteen inner end portions 216 intermittently generates ozone. In addition, occurrence of the corona discharge at any of the annular members 477b can further supplement the volume of ion wind and thus maintain the volume of ion wind generated by the entirety of the counter electrode body 480.

The diameter of the imaginary circle C2 formed by the annular members 477b is longer than the diameter of the imaginary circle C1 formed by the sixteen inner end portions 216. The imaginary circles C1 and C2 are disposed concentrically with each other.

Similarly to the imaginary circle C of the first type of counter electrode bodies, this fourth type of counter electrode bodies is also characterized in that the radius of the imaginary circle C1 is smaller than half the radius of the outer periphery 212. Thus the shapes of the projection members 437a and 477a may be changed as appropriate as long as the radial lengths of the projection members 437a and 477a in the corresponding counter electrode bodies 440 to 480 are at least half the radius of the outer periphery 212.

<<Fifth Type of Counter Electrode Body>>

Figure 18A:
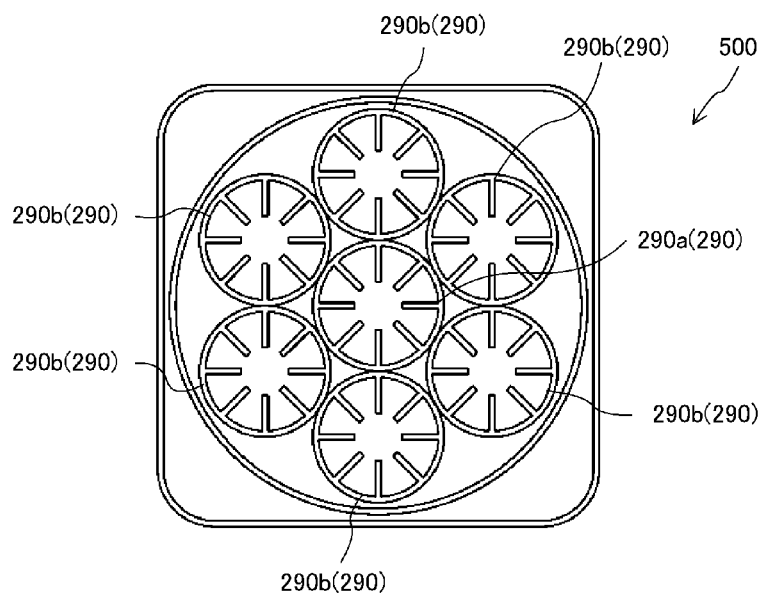
FIG. 18 is a front view illustrating structures of counter electrode bodies 500 and 510.
Figure 18B:
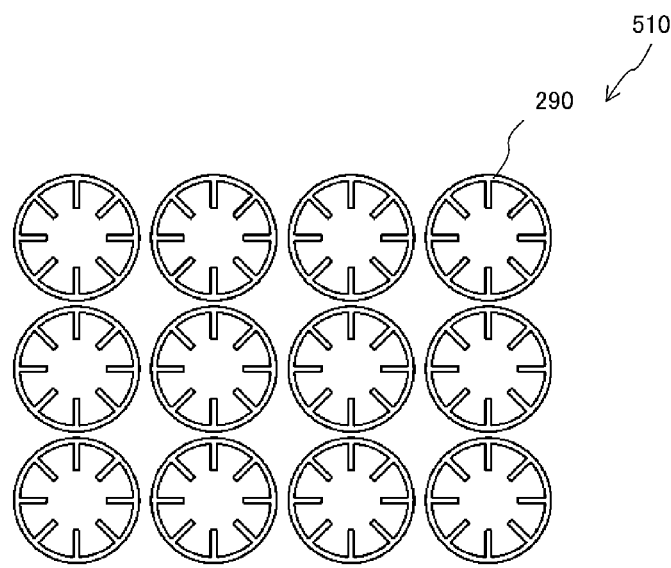

Although the structure of a single counter electrode body has been detailed, the number of the counter electrode bodies is not limited as illustrated in FIGS. 18A and 18B. For example, a counter electrode body 500 illustrated in FIG. 18A has seven counter electrode body 290 having the same shape (substantially annular shape with the same diameter). The second counter electrode bodies 290b are disposed along the outer periphery of the first counter electrode body 290a and adjacent to one another.

More specifically, when a substantially regular hexagonal shape is assumed, the second counter electrode bodies 290b are disposed to be adjacent to one another so that the centers of the six second counter electrode bodies 290b form the vertices of the substantially regular hexagonal shape. The first counter electrode body 290a can be defined to be located in contact with the second counter electrode bodies 290b as well, that is, located at the center of the substantially regular hexagonal shape that is assumed to be formed by the second counter electrode bodies 290b. The second counter electrode bodies 290b need not have a common boundary between the adjoining counter electrode bodies and may be in close proximity therebetween. However, the greater spacing between the adjoining counter electrode bodies may reduce the volume of the ion wind to be generated. Thus each second counter electrode body 290b is preferably such that the distance between the outer peripheries of the adjoining counter electrode bodies, particularly the shortest distance therebetween, is equal to or less than the diameter of the second counter electrode body 290b or is equal to or less than 1/n of the diameter thereof, wherein n is a natural number. The first counter electrode body 290a need not be in contact with all the second counter electrode bodies 290b and may be in close proximity therewith. Preferably, the first counter electrode body 290a is in contact with at least one of the second counter electrode bodies 290b. In this case as well, preferably, the shortest distance between the outer peripheries is equal to or less than the diameter of the first counter electrode body 290a or the second counter electrode body 290b or is equal to or less than 1/n of the diameter thereof, wherein n is a natural number.

As illustrated in FIG. 18B, a total of twelve counter electrode bodies 290 having an array of three rows and four columns may be arranged in a plane.

<<Discharge Electrode Body 150>>

Next, the configuration of the discharge electrode body 150 of the present invention is described.

The shape or the number of the discharge electrode body 150 according the present embodiment is not particularly limited as long as the corona discharge occurs between the discharge electrode body 150 and the above-described various types of the counter electrode bodies. For example, the discharge electrode body 150 can be an electrode body having a single needle-shaped portion.

Furthermore, the discharge electrode body 150 may be an electrode body having multiple needle-shaped portions. In accordance with the number, the shape, or the arrangement of the counter electrode body, the needle-shaped portions may be disposed at position where the corona discharge is more likely to occur. For example, in the example illustrated in FIG. 18A, the electrode body may be provided having seven needle-shaped portions each directed toward the center of the corresponding one of the seven counter electrode bodies 290. In the example illustrated in FIG. 18B, the electrode body may be disposed having twelve needle-shaped portions each directed toward the center of the corresponding one of the twelve counter electrode bodies 290.

When the electrode has such a needle-shaped portion, the tip of the portion is preferably sharp. The sharp tip can cause more likely occurrence of the discharge.

The electrode body having a disc shape or an annular shape instead of the needle shape may be used as the discharge electrode body 150.

When the electrode has such a disc shape or an annular shape, the portion on the outer periphery side is preferably sharp. That is, the electrode is preferably shaped in a knife-edge (having an acute angle) so that the thickness gradually decreases toward the outer side. Providing sharpness to the outer periphery side can cause the more likely occurrence of the discharge at any portion of the outer periphery, which can improve discharge efficiency.

When the electrode has an annular shape, the annular shape may be formed using a thin metal wire or the like. Use of the electrical conductor such as the thin metal wire including a piano wire can cause the more likely occurrence of the discharge at any portion of the outer periphery similarly to the electrode shaped in a knife-edge, which can improve discharge efficiency.

Preferably, the discharge electrode body 150 and the counter electrode body are arranged such that the axis defined by the discharge electrode body 150 is positioned to align with the axis defined by the counter electrode body. This can increase the places where the discharge is more likely to occur and improve discharge efficiency.

As described above, the discharge electrode body 150 may have any shape, arrangement, and number as long as the discharge electrode body can define an axis extending along a predetermined direction. For example, when the discharge electrode body 150 has an elongated shape, the direction of the axis may be a longitudinal direction of the discharge electrode body. When the discharge electrode body 150 has symmetry, the axis of symmetry can be the axis of the discharge electrode body 150. The symmetry can be axial symmetry, point symmetry, rotational symmetry, or the like. For example, when the discharge electrode body has a disc shape or an annular shape, the axis may be an axis that passes through the center or the center of gravity of the counter electrode body and extends vertically relative to a plane including the disc and the ring.

Furthermore, the axis is not required to pass through the center or the like of the discharge electrode body 150. The axis may be shifted from the center of the discharge electrode body as long as the axis is associated with features of the shape or arrangement of the discharge electrode body 150.

Thus the discharge electrode body 150 may have any shape and arrangement that can define the axis, and is not limited to a particular shape or number.

<<Formation of Imaginary Circle C and Corona Discharge>>

As described above, the corona discharge occurs at the counter electrode bodies 210 to 510. The counter electrode bodies 210 to 510 have the inner end portions 216, and the more likely occurrence of the corona discharge depends on the shape of the inner end portions 216.

<Inner End Portions 216 Formed to have an Acute Angle>

Figure 19:
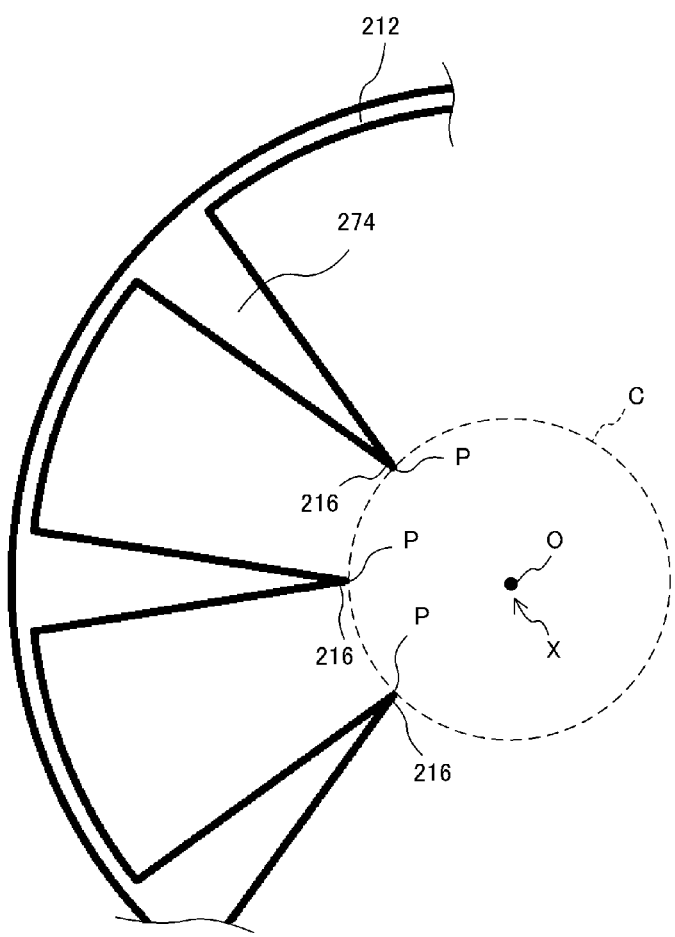
FIG. 19 is a partial front view illustrating inner end portions 216 formed to have an acute angle.

As illustrated in FIG. 19, when the inner end portions 216 are formed to have an acute angle, the distances between the discharge electrode body 150 and the acute tip portions P are the shortest, and the distances between the discharge electrode body 150 and the positions other than the tip portions P of the inner end portions 216 are longer. From the relationship between the shape of the inner end portions 216 and the distance from the discharge electrode body 150, corona discharge is most likely to occur at the tip portions P, and compared with the occurrence at the tip portions P, the corona discharge is less likely to occur at the positions other than the tip portions P. Specifically, the corona discharge is less likely to occur as the position is farther away from the tip portions P to be located at a longer distance between that position and the discharge electrode body 150.

Thus, forming the inner end portions 216 to have an acute angle provides selective occurrence of the corona discharge at the tip portions P. Such a more likely occurrence of the corona discharge at the tip portions P more likely generates ozone near the tip portions P.

When the inner end portions 216 are formed to have an acute angle, imaginary smooth connection of the tip portions P of the respective inner end portions 216 from one after another forms an imaginary circle C having the center O as illustrated in FIG. 19. The distances between the discharge electrode body 150 and all the positions on the circumference of the imaginary circle C are the same, but the only portions on the circumference of the imaginary circle C at which the projection members 214 and the like exist are the tip portions P. Thus the only positions on the circumference of the imaginary circle C at which the corona discharge occurs are the tip portions P, and intermittent occurrence of ozone can reduce the ozone concentration.

<Inner End Portions 216 Having a Convexly Curved Shape>

Figure 20:
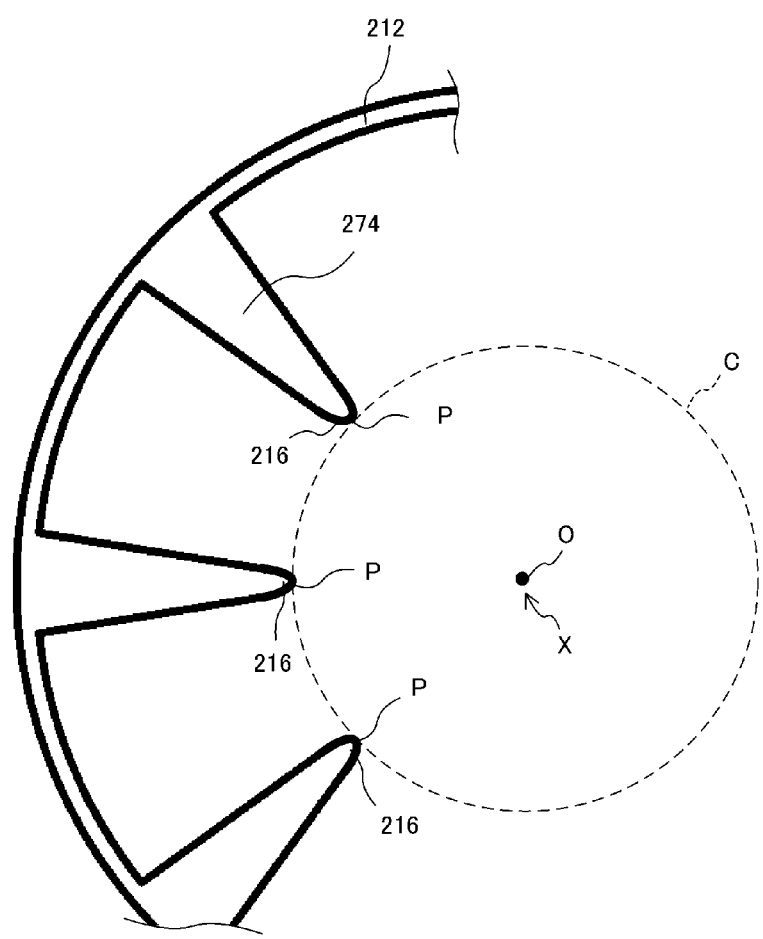
FIG. 20 is a partial front view illustrating inner end portions 216 having a convexly curved shape.

As illustrated in FIG. 20, when the inner end portions 216 have a convexly curved shape, the distances between the discharge electrode body 150 and the positions of the most protruded portions P of the curved surfaces are the shortest, and the distances between the discharge electrode body 150 and the positions other than the protruded portions P of the inner end portions 216 are longer. From the relationship between the shape of the inner end portions 216 and the distance from the discharge electrode body 150, corona discharge is most likely to occur at the protruded portions P, and compared with the occurrence at the protruded portions P, the corona discharge is less likely to occur at the positions other than the protruded portions P. Specifically, the corona discharge is less likely to occur as the position is farther away from the protruded portions P to be located at a longer distance between that position and the discharge electrode body 150.

Thus, forming the inner end portions 216 to have a convexly curved shape provides selective occurrence of the corona discharge at the protruded portions P. Such a more likely occurrence of the corona discharge at the protruded portions P more likely generates ozone near the protruded portions P.

When the inner end portions 216 are formed to have a convexly curved shape, imaginary smooth connection of the protruded portions P of the respective inner end portions 216 from one after another forms an imaginary circle C having the center O as illustrated in FIG. 20. The distances between the discharge electrode body 150 and all the positions on the circumference of the imaginary circle C are the same, but the only portions on the circumference of the imaginary circle C at which the projection members 214 and the like exist are the protruded portions P. Thus the only positions on the circumference of the imaginary circle C at which the corona discharge occurs are the protruded portions P, and intermittent occurrence of ozone can reduce the ozone concentration.

<Inner End Portions 216 having Flat Surfaces>

Figure 21:
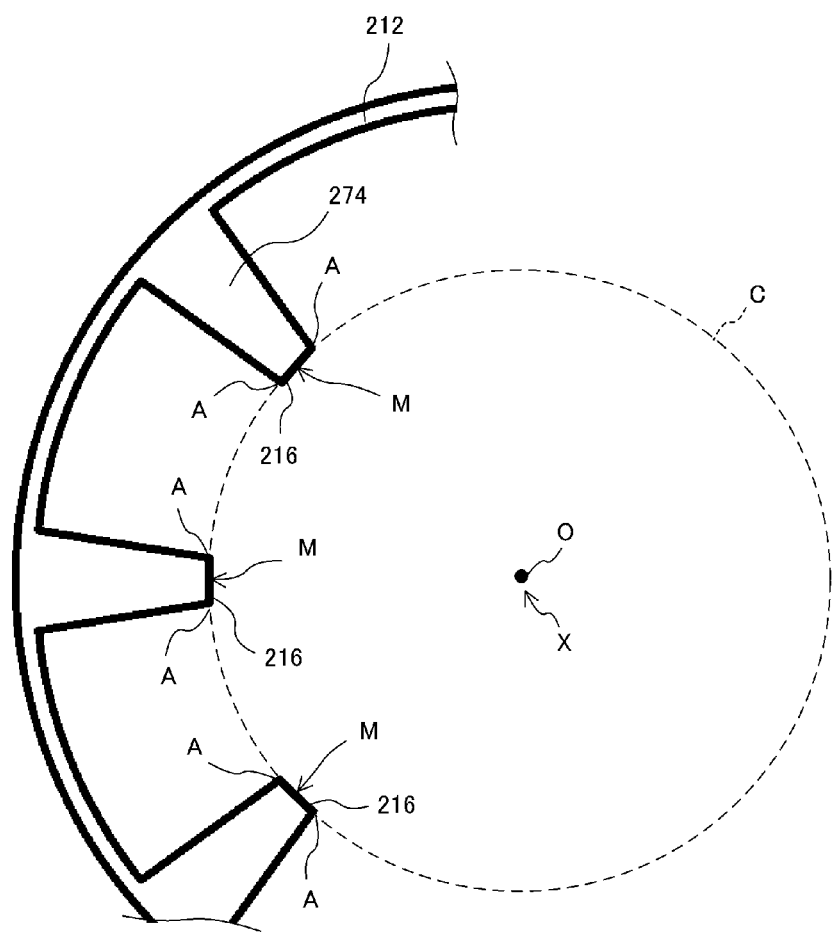
FIG. 21 is a partial front view illustrating inner end portions 216 having flat surfaces.

When the inner end portions 216 have flat surfaces as illustrated in FIG. 21, corona discharge is more likely to occur at a predetermined position on the flat surface. For example, corona discharge may occur at two edges A of the inner end portion 216 or at the middle point M on the flat surface. The two edges A are formed to have a substantially right angle, and an electric field that causes the corona discharge to be more likely to occur is produced around the two edges A. The distance between the discharge electrode body 150 and the middle point M of the flat surface is the shortest, and the distances between the discharge electrode body 150 and the positions other than the middle point M of the inner end portion 216 are longer.

As described above, the corona discharge is more likely to occur at the two edges A and the middle point M and less likely to occur at the portions other than the edges A and the middle point M. Specifically, the corona discharge is less likely to occur as the position is farther away from the edges A and the middle point M to be located at a longer distance between that position and the discharge electrode body 150.

Thus, forming the inner end portions 216 to have flat surfaces provides occurrence of the corona discharge at positions such as edges A and the middle point M. More likely occurrence of the corona discharge at the edges A and the middle point M more likely generates ozone near the edges A and the middle point M.

When the inner end portions 216 are formed to have flat surfaces, imaginary smooth connection of the two edges A of the respective inner end portions 216 from one after another forms an imaginary circle C having the center O as illustrated in FIG. 21. The positions on the circumference of the imaginary circle C at which the projection members 214 and the like exist are the edges A. Thus the positions on the circumference of the imaginary circle C at which the corona discharge occurs are the edges A, and intermittent occurrence of ozone at the edges A can reduce the ozone concentration.

The imaginary circle C may be formed by imaginary smooth connection of the middle points M of the respective inner end portions 216 instead of the two edges A. The imaginary circle C may be formed to include the positions at which the corona discharge is most likely to occur.

Even if the corona discharge occurs both at the edges A and the middle point M, ozone is generated intermittently, which can reduce the ozone concentration.

<Inner End Portions 216 Having a Concavely Curved Shape>

Figure 22:
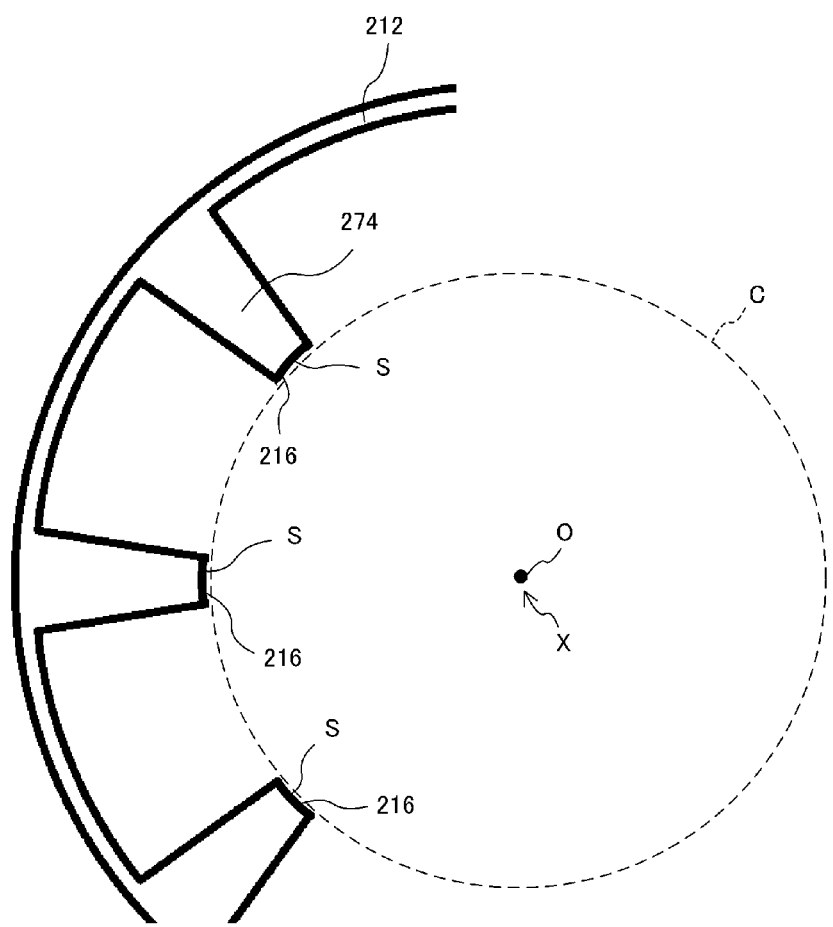
FIG. 22 is partial front view illustrating inner end portions 216 having a concavely curved shape.

As illustrated in FIG. 22, when the inner end portions 216 have a concavely curved shape that forms a part of a spherical surface, the distances between the discharge electrode body 150 and the entire curved surfaces S are the shortest, and the distances between the discharge electrode body 150 and the positions other than the curved surfaces S of the inner end portions 216 are longer. From the relationship between the shape of the inner end portions 216 and the distance from the discharge electrode body 150, corona discharge is more likely to occur at any of curved surfaces S, and compared with the occurrence at the curved surfaces S, the corona discharge is less likely to occur at the positions other than the curved surfaces S. Specifically, the corona discharge is less likely to occur as the position is farther away from the curved surfaces S to be located at a longer distance between that position and the discharge electrode body 150.

Thus, forming the inner end portions 216 to have concavely curved surfaces that form a part of a spherical surface provides selective occurrence of the corona discharge at the curved surfaces S. More likely occurrence of the corona discharge at the curved surfaces S more likely generates ozone near the curved surfaces S.

When the inner end portions 216 are formed to have a concavely curved shape that forms a part of the spherical surface, imaginary smooth connection of the curved surfaces S of the respective inner end portions 216 from one after another forms an imaginary circle C having the center O as illustrated in FIG. 22. The distances between the discharge electrode body 150 and all the positions on the circumference of the imaginary circle C are the same, but the only portions on the circumference of the imaginary circle C at which the projection members 214 and the like exist are the curved surfaces S. Thus the only positions on the circumference of the imaginary circle C at which the corona discharge occurs are the curved surfaces S, and intermittent occurrence of ozone can reduce the ozone concentration.

Second Embodiment

In the ion wind generation device 110 according to the above-described first embodiment, the description has been made of the configuration that the discharge electrode body 150 faces one side (front side) of the counter electrode body 210 and the like, and ion wind is generated from the one side (front side) toward the other side (back side) of the counter electrode body 210 and the like. Such an overall unidirectional flow of ion wind from the front side toward the back side enables the ion wind to be scattered farther. However, when the ion wind is desirably to be scattered to spread over in a substantially radial direction (over 360 degrees) in a space, another configuration different from the ion wind generation device 110 according to the first embodiment may be preferable.

Such an ion wind generation device is described hereinafter as a second embodiment. As illustrated in FIGS. 23 to 25, an ion wind generation device 120 according to the present inventions includes a discharge electrode body 160 and an annular counter electrode body 610 having a plurality of projection members 614. The discharge electrode body 160 is disposed concentrically with the annular counter electrode body 610.

Here, the projection members 614 have inner end portions 616 that are tips located on the annular center side of the counter electrode body 610. Imaginary smooth connection of the inner end portions 616 of the adjacent projection members 614 forms an imaginary circle C in the same plane as the counter electrode body 610 at the central portion of the counter electrode body 610.

As illustrated in FIGS. 23 to 25, the discharge electrode bodies 160 and 170 according to the second embodiment have a disc shape. The outer periphery of the discharge electrode body 160 is shaped to have an edged shape (shape formed to have an acute angle) having a thickness gradually thinner toward the outer side. Discharge electrode body 160 can discharge from the edged outer periphery.

The counter electrode bodies 610, 620, and 630 of the second embodiment mainly use the second type of counter electrode body of the first embodiment. The first type, the third type, or the fourth type of the counter electrode body of the first embodiment may be used as the counter electrode bodies 610, 620, and 630 of the second embodiment.

<Counter Electrode Body 610>

As illustrated in FIG. 23, the counter electrode body 610 has plate-like projection members 614, and the projection members 614 have a substantially trapezoidal shape. As described in the first embodiment, the projection members 614 may have any plate-like shape, and may have various shapes such as a rectangular shape and a fan shape. The substantially trapezoidal projection members 614 are located circumferentially in the annular outer periphery 212.

Use of the discharge electrode body 160 and the counter electrode bodies 610 illustrated in FIG. 23 can cause corona discharge to selectively occur between the outer periphery of the discharge electrode body 160 and the inner end portions 616 of the projection members 614. This occurrence of the corona discharge can cause ion wind to be generated so as to spread over in the radial direction of the discharge electrode body 160 and the counter electrode body 610.

Figures 23A, 23B:
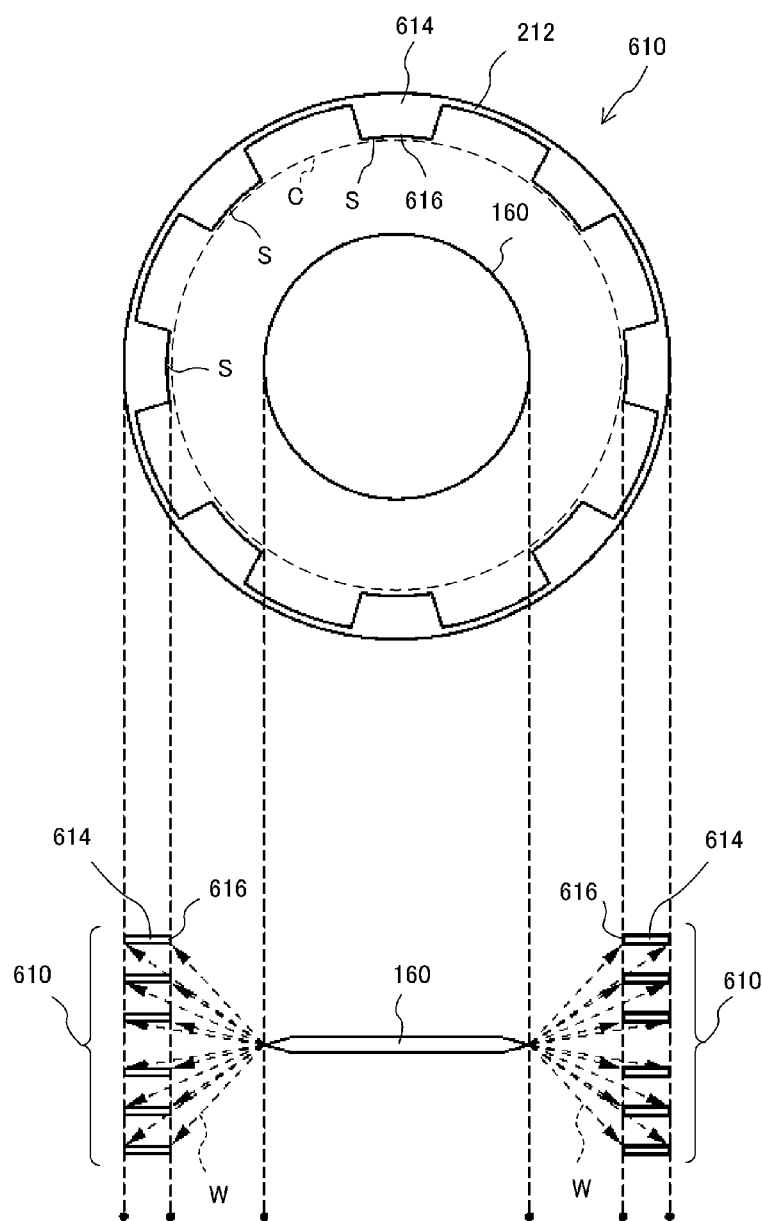
FIG. 23 is a front view illustrating a structure of a counter electrode body 610.

As illustrated in FIG. 23B, the second embodiment has a stack of counter electrode bodies 610. FIG. 23B illustrates an example of a stack of six counter electrode bodies 610. This structure can cause corona discharge to selectively occur between the outer periphery of the discharge electrode body 160 and the inner end portion 616 of any of the projection members 614 of the six counter electrode bodies 610. This structure can also provide appropriate adjustment of positions where the corona discharge occurs and scattering of ion wind W so as to achieve a desired volume of wind.

<Imaginary Circle C and Reduction in Ozone Concentration>

As illustrated in FIG. 23A, when the inner end portions 616 have a concavely curved shape that forms a part of a spherical surface, the distances between the discharge electrode body 160 and the entire curved surfaces S are the shortest, and the distances between the discharge electrode body 160 and the positions other than the curved surfaces S of the inner end portions 616 are longer. From the relationship between the shape of the inner end portions 616 and the distance from the discharge electrode body 160, corona discharge is more likely to occur at any of curved surfaces S, and compared with the occurrence at the curved surfaces S, the corona discharge is less likely to occur at the positions other than the curved surfaces S. Specifically, the corona discharge is less likely to occur as the position is farther away from the curved surfaces S to be located at a longer distance between that position and the discharge electrode body 160.

Thus, forming the inner end portions 616 to have concavely curved surfaces that form a part of a spherical surface provides selective occurrence of the corona discharge at the curved surfaces S. More likely occurrence of the corona discharge at the curved surfaces S more likely generates ozone near the curved surfaces S.

When the inner end portions 616 are formed to have a concavely curved shape that forms a part of the spherical surface, imaginary smooth connection of the curved surfaces S of the respective inner end portions 616 from one after another forms an imaginary circle C as illustrated in FIG. 23A. The distances between the discharge electrode body 160 and all the positions on the circumference of the imaginary circle C are the same, but the only portions on the circumference of the imaginary circle C at which the projection members 614 and the like exist are the curved surfaces S. Thus the only positions on the circumference of the imaginary circle C at which the corona discharge occurs are the curved surfaces S, and intermittent occurrence of ozone can reduce the ozone concentration.

<Counter Electrode Body 620>

As illustrated in FIG. 24, the counter electrode bodies 620 have plate-like projection members 614, and the projection members 614 have a substantially trapezoidal projection member 614a and a substantially semi-elliptical projection member 614b. The substantially trapezoidal shaped-projection members 614a and the substantially semi-elliptical projection member 614b are alternately located circumferentially in the annular outer periphery 212.

In the outer periphery 172 of the discharge electrode body 170, protruded portions 174 protruding toward the outer side are formed circumferentially. The discharge electrode body 170 can discharge from the tips of the protruded portions 174.

Use of the discharge electrode body 170 and the counter electrode bodies 620 illustrated in FIG. 24 can cause corona discharge to selectively occur between the tips of the protruded portions 174 in the outer periphery 172 of the discharge electrode body 170 and the inner end portions 616 of the projection members 614a and 614b. This occurrence of the corona discharge can cause ion wind W to be generated so as to spread over in the radial direction of the discharge electrode body 170 and the counter electrode body 620.

Figures 24A, 24B:
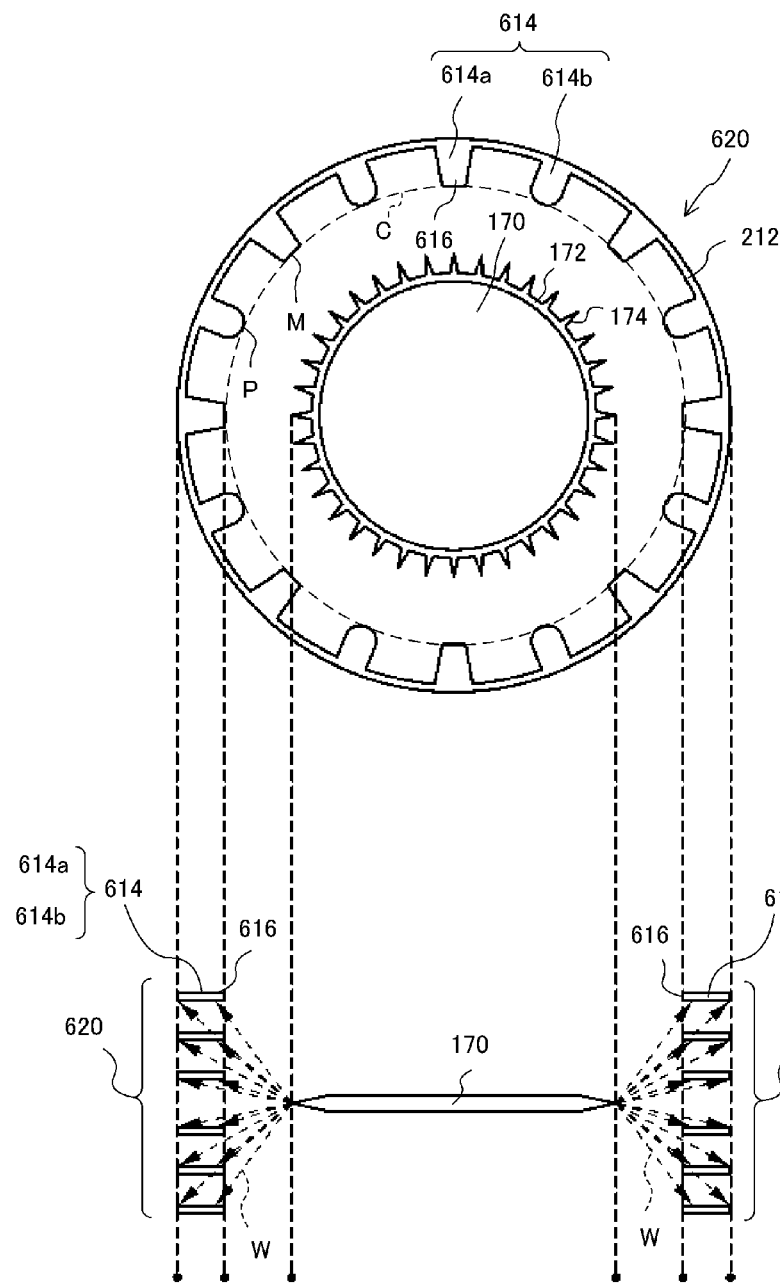
FIG. 24 is a front view illustrating a structure of a counter electrode body 620.

As illustrated in FIG. 24B, the second embodiment has a stack of counter electrode bodies 620. FIG. 24B illustrates an example of a stack of six counter electrode bodies 620. This structure can cause corona discharge to selectively occur between the tips of the protruded portions 174 of the discharge electrode body 170 and the inner end portion 616 of any of the projection members 614a and 614b of the six counter electrode bodies 620. This structure can also provide appropriate adjustment of positions where the corona discharge occurs and scattering of ion wind W so as to achieve a desired volume of wind.

<Imaginary Circle C and Reduction in Ozone Concentration>

As illustrated in FIG. 24A, the projection members 614 have a substantially trapezoidal projection member 614a and a substantially semi-elliptical projection member 614b.

Corona discharge is more likely to occur at a predetermined position on a flat surface of the projection member 614a. For example, corona discharge may occur at two edges A of the projection member 614a or at the middle point M or the like on the flat surface. The two edges A are formed to have a substantially right angle, and an electric field that causes the corona discharge to be more likely to occur is produced around the two edges A. The distance between the discharge electrode body 170 and the middle point M of the flat surface is the shortest, and the distances between the discharge electrode body 170 and the positions other than the middle point M of the projection member 614a are longer.

As described above, the corona discharge is more likely to occur at the two edges A and the middle point M and less likely to occur at the portions other than the edges A and the middle point M. Specifically, the corona discharge is less likely to occur as the position is farther away from the edges A and the middle point M to be located at a longer distance between that position and the discharge electrode body 170.

Thus, forming the projection member 614a to have flat surfaces provides occurrence of the corona discharge at positions such as edges A and the middle point M. More likely occurrence of the corona discharge at the edges A and the middle point M more likely generates ozone near the edges A and the middle point M.

Imaginary smooth connection of the two edges A of the respective projection members 614a from one after another forms an imaginary circle C having the center O as illustrated in FIG. 24A. The positions on the circumference of the imaginary circle C at which the projection members 214 and the like exist are the edges A. Thus the positions on the circumference of the imaginary circle C at which the corona discharge occurs are the edges A, and intermittent occurrence of ozone at the edges A can reduce the ozone concentration.

Corona discharge is also more likely to occur at the positions of the most protruded portions P of the projection members 614b. Even if the corona discharge occurs at not only the edges A but also the middle point M or the protruded portions P, ozone is generated intermittently, which can reduce the ozone concentration.

The discharge electrode body 170 has protruded portions 174, and a more likely occurrence of the corona discharge is also determined by the distances between the discharge electrode body 170 and the protruded portions 174. Similarly, the intermittent occurrence of ozone reduces the ozone concentration.

<Counter Electrode Body 630>

As illustrated in FIG. 25, the counter electrode body 630 has plate-like projection members 614, and the projection members 614 have a substantially fan shape.

The substantially fan-shaped projection members 614 are located circumferentially in the annular outer periphery 212.

Use of the discharge electrode body 160 and the counter electrode bodies 630 illustrated in FIG. 25 can cause corona discharge to intermittently (selectively) occur between the outer periphery of the discharge electrode body 160 and the inner end portions 616 of the substantially fan-shaped projection members 614. This occurrence of the corona discharge can cause ion wind W to be generated so as to spread over in the radial direction of the discharge electrode body 160 and the counter electrode body 630.

<Imaginary Circle C and Reduction in Ozone Concentration>

Figure 25A:
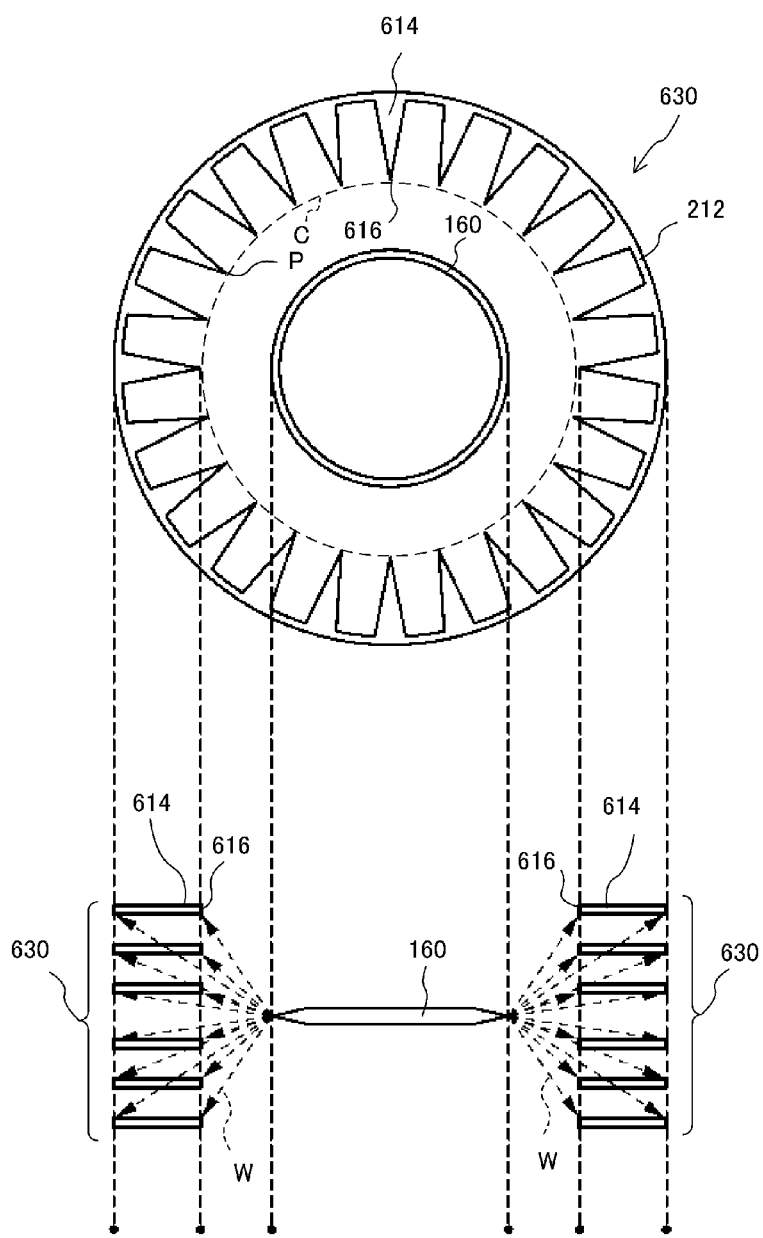
FIG. 25 is a front view illustrating a structure of a counter electrode body 630.
Figure 25B:
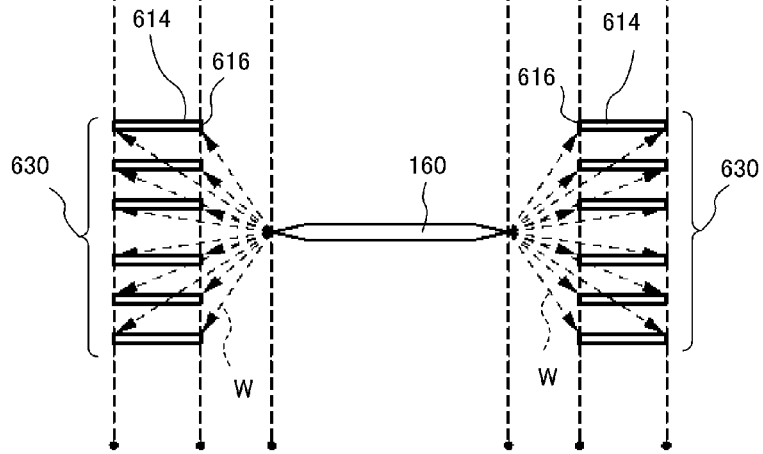

As illustrated in FIG. 25A, when the inner end portions 616 are formed to have an acute angle, the distances between the discharge electrode body 160 and the acute tip portions P are the shortest, and the distances between the discharge electrode body 160 and the positions other than the tip portions P of the inner end portions 616 are longer. From the relationship between the shape of the inner end portions 616 and the distance from the discharge electrode body 160, corona discharge is most likely to occur at the tip portions P, and compared with the occurrence at the tip portions P, the corona discharge is less likely to occur at the positions other than the tip portions P. Specifically, the corona discharge is less likely to occur as the position is farther away from the tip portions P to be located at a longer distance between that position and the discharge electrode body 160.

Thus, forming the inner end portions 616 to have an acute angle provides selective occurrence of the corona discharge at the tip portions P. Such a more likely occurrence of the corona discharge at the tip portions P more likely generates ozone near the tip portions P.

When the inner end portions 616 are formed to have an acute angle, imaginary smooth connection of the tip portions P of the respective inner end portions 216 from one after another forms an imaginary circle C as illustrated in FIG. 25A. The distances between the discharge electrode body 160 and all the positions on the circumference of the imaginary circle C are the same, but the only portions on the circumference of the imaginary circle C at which the projection members 614 and the like exist are the tip portions P. Thus the only positions on the circumference of the imaginary circle C at which the corona discharge occurs are the tip portions P, and intermittent occurrence of ozone can reduce the ozone concentration.

Furthermore, in the second embodiment as well, when corona discharge occurs between the discharge electrode body 160 or 170 and the inner end portions 616 of the annular counter electrode bodies 610, 620, or 630, the ion wind generated at the inner end portions 616 of the counter electrode bodies 610, 620, or 630 is released toward sides of the counter electrode bodies 610, 620, or 630 on which the counter electrode bodies 610, 620, or 630 do not face the discharge electrode body 160 or 170, and negative pressure is generated on the sides of the counter electrode bodies 610, 620, or 630 on which the counter electrode bodies 610, 620, or 630 do not face the discharge electrode body 160 or 170. Air surrounding the counter electrode bodies 610, 620, or 630 is drawn toward the space in which the negative pressure is generated, and the drawn air forces the ion wind toward the sides in which the counter electrode bodies 610, 620, or 630 do not face the discharge electrode body 160 or 170, thereby enabling an increase of power of the ion wind.

In an alternative expression, the ion wind generation device 120 according to the above-described second embodiment can have a configuration in which, in the ion wind generation device 110 according to the first embodiment, the discharge electrode body 160 or 170 shaped to be annular and have a diameter smaller than the imaginary circle C of the counter electrode bodies 210 to 480 is disposed in close proximity in the plane in which the counter electrode bodies 210 to 480 exist. Thus the shape of the counter electrode body 610, 620, or 630 according to the second embodiment can have a shape similar to those of the counter electrode bodies 210 to 480 of the above-described first embodiment.

Third Embodiment

The ion wind generation device 110 according to the first embodiment and the ion wind generation device 120 according to the second embodiment have been described in detail as different embodiments capable of reducing generation of ozone included in the ion wind by providing an annular-like counter electrode body with a particular shape. The following description is an ion wind generation device 130 according to the third embodiment having a non-annular type of counter electrode body.

The above-described example shows that the electrode body of the receiving electrode that is the counter electrode body has a substantially annular shape. The electrode body of the receiving electrode may have a linear shape. In this case, the electrode body of the discharging electrode may also have a linear shape in accordance with the shape of the electrode body of the receiving electrode.

Figure 26A:
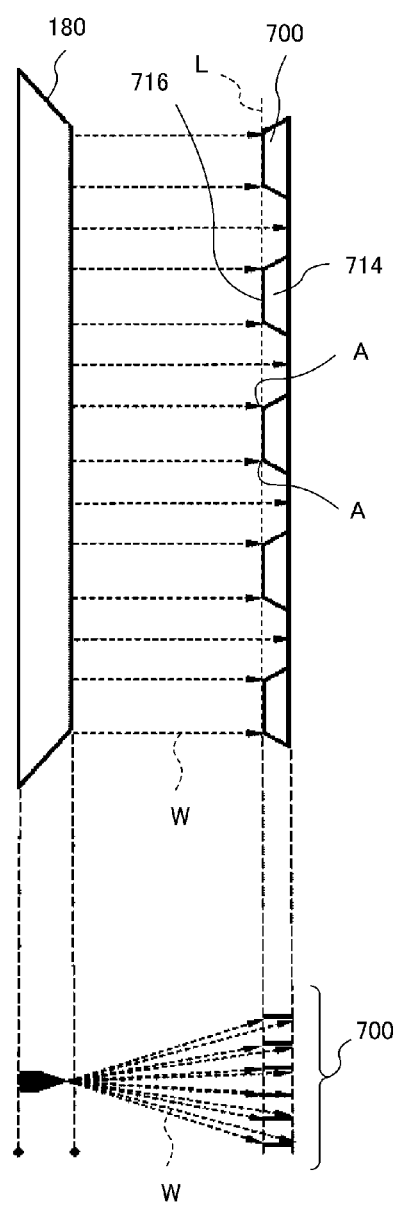
FIG. 26 is a front view illustrating structures of counter electrode bodies 700 and 710.
Figure 26B:
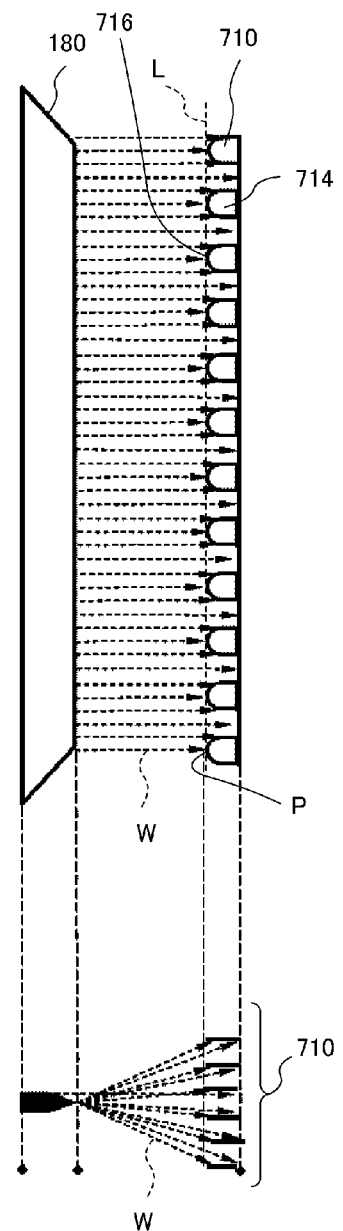

As illustrated in FIGS. 26A and 26B, the ion wind generation device 130 of the present invention includes a discharge electrode body 180 having an end portion formed to be linear and a counter electrode body 700 or 710 having projection members 714 disposed linearly. The discharge electrode body 180 is disposed to face the linear counter electrode body 700 or 710.

The discharge electrode body 180 has a thin-plate shape and a linear side facing the counter electrode body 700 or 710. The side facing the counter electrode body 700 or 710 is preferably shaped in a knife-edge (having an acute angle) so that the thickness gradually decreases toward the outer side. Providing sharpness to the side facing the counter electrode body 700 or 710 can cause the more likely occurrence of the discharge at any position, which can improve discharge efficiency.

The discharge electrode body 180 need not have a thin-plate shape, and may be formed by a linear electrical conductor such as a thin metal wire. Use of the thin metal wire such as a piano wire can cause the more likely occurrence of the discharge at any position similarly to the electrode shaped in a knife-edge, which can improve discharge efficiency.

Here, in the projection members 714, imaginary connection of end portions 716 of the adjoining projection members 714 forms an imaginary line L in the same plane as the counter electrode body 700 or 710.

<Counter Electrode Body 700>

As illustrated in FIG. 26A, the counter electrode bodies 700 have plate-like projection members 714, and the projection members 714 have a substantially trapezoidal shape. As described in the first embodiment, the projection members 714 may have any plate-like shape, and may have various shapes such as a rectangular shape and a fan shape.

Use of the discharge electrode body 180 and the counter electrode bodies 700 illustrated in FIG. 26A can cause corona discharge to intermittently (selectively) occur between the end portion of the discharge electrode body 180 and the end portions 716 of the projection members 714. This occurrence of the corona discharge can cause ion wind to be generated so as to move from the discharge electrode body 180 toward the counter electrode bodies 700 in a zonal manner.

As illustrated in FIG. 26A, the counter electrode bodies 700 according to the third embodiment are a stack of counter electrode bodies. FIG. 26A illustrates an example of a stack of six counter electrode bodies 700. This structure can cause corona discharge to selectively (intermittently) occur between the outer periphery of the discharge electrode body 180 and the end portion 716 of any of the projection members 714 of the six counter electrode bodies 700. This structure can also provide appropriate adjustment of positions where the corona discharge occurs and scattering of ion wind W so as to achieve a desired volume of wind.

<Imaginary Line L and Reduction in Ozone Concentration>

When the end portions 716 have flat surfaces as illustrated in FIG. 26A, corona discharge is more likely to occur at a predetermined position on the flat surface. For example, the corona discharge occurs at two edges A of the end portion 716. An electric field that causes the corona discharge to be more likely to occur is produced around the two edges A. The distance between the discharge electrode body 180 and the two edges A is the shortest, and the distances between the discharge electrode body 180 and the positions other than the two edges A of the end portion 716 are longer.

As described above, the corona discharge is more likely to occur at the two edges A and less likely to occur at the portions other than the edges A. Specifically, the corona discharge is less likely to occur as the position is farther away from the edges A to be located at a longer distance between that position and the discharge electrode body 180.

Thus, forming the end portions 716 to have flat surfaces provides occurrence of the corona discharge at positions such as edges A. More likely occurrence of the corona discharge at the edges A more likely generates ozone near the edges A.

When the end portions 716 are formed to have flat surfaces, imaginary smooth connection of two edges A of one end portion 716 from one after another forms an imaginary line L as illustrated in FIG. 26A. The positions on the imaginary line L at which the corona discharge occurs are edges A, and intermittent occurrence of ozone at the edges A can reduce the ozone concentration.

<Counter Electrode Body 710>

As illustrated in FIG. 26B, the counter electrode bodies 710 have plate-like projection members 714, and the projection members 714 have a substantially semi-elliptical shape.

Use of the discharge electrode body 180 and the counter electrode bodies 710 illustrated in FIG. 26B can cause corona discharge to selectively (intermittently) occur between the end portion of the discharge electrode body 180 and the end portions 716 of the substantially semi-elliptical projection members 714. This occurrence of the corona discharge can cause ion wind to be generated so as to move from the discharge electrode body 180 toward the counter electrode bodies 710 in a thin zonal manner.

As illustrated in FIG. 26B, the counter electrode bodies 710 according to the third embodiment are a stack of counter electrode bodies. FIG. 26B illustrates an example of a stack of six counter electrode bodies 710. This structure can cause corona discharge to intermittently (selectively) occur between the outer periphery of the discharge electrode body 180 and the end portion 716 of any of the projection members 714 of the six counter electrode bodies 710. This structure can also provide appropriate adjustment of positions where the corona discharge occurs and scattering of ion wind W so as to achieve a desired volume of wind.

<Imaginary Line L and Reduction in Ozone Concentration>

As illustrated in FIG. 26B, when the end portions 716 have a convexly curved shape, the distances between the discharge electrode body 180 and the position of the most protruded portions P of the curved surfaces are the shortest, and the distances between the discharge electrode body 180 and the positions other than the protruded portions P of the end portions 716 are longer. From the relationship between the shape of the end portions 716 and the distance from the discharge electrode body 180, corona discharge is most likely to occur at the protruded portions P, and compared with the more likely occurrence at the protruded portions P, the corona discharge is less likely to occur at the positions other than the protruded portions P. Specifically, the corona discharge is less likely to occur as the position is farther away from the protruded portions P to be located at a longer distance between that position and the discharge electrode body 180.

Thus, forming the end portions 716 to have a convexly curved shape provides selective occurrence of the corona discharge at the protruded portions P. Such a more likely occurrence of the corona discharge at the protruded portions P more likely generates ozone near the protruded portions P.

When the end portions 716 are formed to have a convexly curved shape, imaginary smooth connection of the protruded portions P of the respective end portions 716 from one after another forms an imaginary line L as illustrated in FIG. 26B. The distances between the discharge electrode body 180 and all the positions on the imaginary line L are the same, but the only portions on the imaginary line L at which the projection members 714 and the like exist are the protruded portions P. Thus the only positions in the end portions 716 at which the corona discharge occurs are the protruded portions P, and intermittent occurrence of ozone can reduce the ozone concentration.

REFERENCE SIGNS LIST

110 ION WIND GENERATION DEVICE 110
150 DISCHARGE ELECTRODE BODY
210 COUNTER ELECTRODE BODY
270 COUNTER ELECTRODE BODY

320 COUNTER ELECTRODE BODY
430 COUNTER ELECTRODE BODY
610 COUNTER ELECTRODE BODY
700 COUNTER ELECTRODE BODY

The invention claimed is:

1. An ion/ozone wind generation device for generating ion/ozone wind by corona discharge, the ion/ozone wind generation device comprising:
an electrode pair including
a discharge electrode body having a circular periphery around an axis and a discharge portion at an edge of the discharge electrode body, and
a counter electrode body having an annular outer periphery that is formed around a center of the counter electrode body, and a plurality of projections extending from the outer periphery toward thereinside, each of the projections being formed with two portions that are an end portion and a non-end portion wherein the end portion is defined by a distal end of the projection and the non-end portion is defined by a remaining portion other than the distal end, the corona discharge occurring due to a potential difference generated between the discharge portion and the counter electrode body, wherein
the end portions of the projections are located spaced apart from one another in a single plane and around the center of the counter electrode body in the single plane,
the discharge portion of the discharge electrode body is not disposed in the single plane in which the counter electrode body is disposed and
the axis of the discharge electrode body is disposed at the center of the counter electrode body such that the discharge portion of the discharge electrode body and the outer periphery of the counter electrode body are concentrically arranged,
seen from a view from the axis of the discharge portion, the discharge portion is located inside all the projections,
a distance between the end portion of each projection and the discharge portion is shorter than a distance between the non-end portion of each projection and the discharge portion.

2. The ion/ozone wind generation device according to claim 1, wherein
each of the projections extends further toward the center of the outer periphery of the counter electrode body, and
each of the projections has a length equal to or greater than at least half of a radius of the counter electrode body wherein the radius is determined from the center of the counter electrode body to the outer periphery.

3. The ion/ozone wind generation device according to claim 1, wherein the ion/ozone wind generation device is not provided with a fan.

4. The ion/ozone wind generation device according to claim 1, wherein adjoining ones of the projections are disposed spaced at 45 degree or 90 degree intervals from one another along the circumferential direction.

5. The ion/ozone wind generation device according to claim 1, wherein the end portions of the projections are located on a single circumference, which is drawn with a consistent radius on the single plane around the center of the counter electrode body.

6. The ion/ozone wind generation device according to claim 1, wherein
the discharge electrode body has a needle-shaped electrode body, extending in the axis, and
the edge of the discharge electrode body is at a distal end of the needle-shaped discharge electrode body such that the corona discharge occurs at the distal end.

7. The ion/ozone wind generation device according to claim 1, wherein a surface area of the projections is larger than a surface area of the discharge portion so that
the corona discharge is to occur at the end portions of the projections than at the non-end portions thereof, and
a concentration of ozone generated by an entirety of the counter electrode body is reduced by an occurrence of the corona discharge based on the distance between the end portion of each projection and the discharge portion and by an occurrence of the corona discharge based on the distance between the non-end portion of each projection and the discharge portion.

8. The ion/ozone wind generation device according to claim 1, wherein
the discharge electrode body is in either a flat disk shape or a flat ring shape, existing on a flat plane,
the flat plane is parallel to the single plane of the counter electrode body with a certain gap, and
the edge of the discharge electrode body is at an outer rim of either the disk shape or the ring shape such that the corona discharge occurs at the outer rim.

9. The ion/ozone wind generation device according to claim 8, further comprising:
one or more of counter electrode bodies that are identical to the counter electrode bodies in their shape, each of which existing on a different single plane,
each of the counter electrode bodies are arranged parallel to the other counter electrode bodies with an interval in a perpendicular direction of their single planes.

10. The ion/ozone wind generation device according to claim 8, wherein
the outer rim of the discharge electrode body has a plurality of protruded portions that are arranged with an equal interval along the outer rim, the protruded portions extending outwardly.

11. An ion/ozone wind generation device for generating ion/ozone wind by corona discharge, the ion/ozone wind generation device comprising:
a discharge electrode body having a circular periphery around an axis and a discharge portion at an edge of the discharge electrode body, and
a counter electrode body having an annular outer periphery that is formed around a center of the counter electrode body, and a plurality of projections extending from the outer periphery toward thereinside wherein the outer periphery has a consistent radius determined from the center to the outer periphery, each of the projections being formed with two portions that are an end portion and a non-end portion wherein the end portion is defined by a distal end of the projection and the non-end portion is defined by a remaining portion other than the distal end, the corona discharge occurring due to a potential difference generated between the discharge portion and the counter electrode body, wherein
the end portions of the projections are located spaced apart from one another in a single plane and are disposed around the center of the counter electrode body in the single plane,
the discharge portion of the discharge electrode body is not disposed in the single plane in which the counter electrode body is disposed, and
the axis of the discharge electrode body is disposed at the center of the counter electrode body such that the discharge portion of the discharge electrode body and the outer periphery of the counter electrode body are concentrically arranged, seen from a view from the axis of the discharge portion, the discharge portion is located inside all the projections, each of the projections extends toward the center of the outer periphery of the counter electrode body such that the outer periphery is distant from the center by a radius, and each of the projections has a length equal to or greater than at least half of the radius of the counter electrode body.

12. The ion/ozone wind generation device according to claim 11, wherein the ion/ozone wind generation device is not provided with a fan.

13. The ion/ozone wind generation device according to claim 11, wherein adjoining ones of the projections are disposed spaced at 45 degree or 90 degree intervals from one another along a circumferential direction around the center of the counter electrode body.

14. The ion/ozone wind generation device according to claim 11, wherein the end portions of the projections are located on a single circumference, which is drawn with a consistent radius on the single plane around the center of the counter electrode body.

15. The ion/ozone wind generation device according to claim 11, wherein the discharge electrode body has a needle-shaped electrode body extending in the axis, and the edge of the discharge electrode body is at a distal end of the needle-shaped discharge electrode body such that the corona discharge occurs at the distal end.

16. The ion/ozone wind generation device according to claim 11, wherein the discharge electrode body is in either a flat disk shape or a flat ring shape, existing on a flat plane, the flat plane is parallel to the single plane of the counter electrode body with a certain gap, the edge of the discharge electrode body is at an outer rim of either the disk shape or the ring shape such that the corona discharge occurs at the outer rim.

17. An ion/ozone wind generation device for generating ion/ozone wind by corona discharge, the ion/ozone wind generation device comprising:

an electrode pair including a discharge electrode body that is in a thin-plate shape with a linear edge, having a discharge portion on the linear edge, and a counter electrode body having a linear outer edge portion and a plurality of projections, which are aligned on the linear outer edge portion, each of the projections extending from the outer edge portion, and being formed with two portions that are an end portion and a non-end portion wherein the end portion is defined by a distal end of the projection and the non-end portion is defined by a remaining portion other than the distal end, the corona discharge occurring due to a potential difference generated between the discharge portion and the counter electrode body, wherein the end portions of the projections are located spaced apart from one another in a single plane, the discharge electrode body is arranged on a flat plane such that the linear edge on which the discharge portion is placed faces the projections, the flat plane being parallel to the single plane with a certain gap, the discharge portion is formed either in a thin-plate and knife-edged shape or formed by a linear electrical conductor, each of the projections extends in a direction farther from the outer edge portion, a distance between the end portion of each projection and the discharge portion is shorter than a distance between the non-end portion of each projection and the discharge portion so that, the corona discharge is to occur at the end portions of the projections than at the non-end portions thereof, and a concentration of ozone generated by an entirety of the counter electrode body is reduced by an occurrence of the corona discharge based on the distance between the end portion of each projection and the discharge portion and by an occurrence of the corona discharge based on the distance between the non-end portion of each projection and the discharge portion.

18. The ion/ozone wind generation device according to claim 17, wherein seen from a top view that is perpendicular to the single plane, the linear edge of the discharge electrode body is parallel to an imaginary line (L) that is drawn by connecting distal ends of the projections of the counter electrode body.

* * * * *